(12) United States Patent
Vane et al.

(10) Patent No.: US 6,755,975 B2
(45) Date of Patent: Jun. 29, 2004

(54) SEPARATION PROCESS USING PERVAPORATION AND DEPHLEGMATION

(75) Inventors: Leland M. Vane, Cincinnati, OH (US); Anurag P. Mairal, Fremont, CA (US); Alvin Ng, Palo Alto, CA (US); Franklin R. Alvarez, Cincinnati, OH (US); Richard W. Baker, Palo Alto, CA (US)

(73) Assignees: Membrane Technology and Research, Inc., Menlo Park, CA (US); The United States of America as represented by the Environmental Protection Agency, Washington, DC (US)

( * ) Notice: Subject to any disclaimer, the term of this patent is extended or adjusted under 35 U.S.C. 154(b) by 199 days.

(21) Appl. No.: 10/170,333

(22) Filed: Jun. 12, 2002

(65) Prior Publication Data

US 2004/0000521 A1 Jan. 1, 2004

(51) Int. Cl.$^7$ ................................................. C02E 1/44
(52) U.S. Cl. ............................. 210/640; 95/50; 95/45; 95/41; 203/12; 203/18; 203/19
(58) Field of Search ............................. 210/640; 95/45, 95/50, 41; 203/12, 18, 19

(56) References Cited

U.S. PATENT DOCUMENTS

| | | | |
|---|---|---|---|
| 4,755,299 A | 7/1988 | Bruschke | ............ 210/640 |
| 4,900,402 A | 2/1990 | Kaschemekat et al. | |
| 4,925,562 A | 5/1990 | te Hennepe et al. | |
| 5,030,356 A | 7/1991 | Blume et al. | ............ 210/640 |
| 5,354,547 A | * 10/1994 | Rao et al. | ............ 423/650 |
| 6,318,119 B1 | * 11/2001 | Fischer et al. | ............ 62/620 |

OTHER PUBLICATIONS

M. Marin et al., "Separation of Volatile Organic Compounds from Aqueous Mixtures by Pervaporation with Multi–Stage Condensation," J. Food Eng., 28, p. 225–238 (1996).
S. Di Cave et al., "Mathematical Model for Process Design and Simulation of Dephlegmators (Partial Condensers) for Binary Mixtures," Canadian J. of Chem. Eng., 65, p. 559–564 (1987).
G. Lucadamo et al., "Improved Ethylene and LPG Recovery Through Dephlegmator Technology," Gas Purif. and Sep. vol. 1, p. 94–102 (1987).
R. Jibb et al., "The Potential for Using Heat Transfer Enhancement in Vent and Reflux Condensers," (unpublished article available on Internet at http://www.calgavin.co.uk/news) (1999).
J. Caro et al., "Zeolite membranes—state of their development and perspective," Microporous and Mesoporous Materials, 38, p. 3–24 (2000).

* cited by examiner

*Primary Examiner*—Ana M. Fortuna
(74) *Attorney, Agent, or Firm*—J. Farrant

(57) ABSTRACT

A process for treating liquids containing organic compounds and water. The process includes a pervaporation step in conjunction with a dephlegmation step to treat at least a portion of the permeate vapor from the pervaporation step. The process yields a membrane residue stream, a stream enriched in the more volatile component (usually the organic) as the overhead stream from the dephlegmator and a condensate stream enriched in the less volatile component (usually the water) as a bottoms stream from the dephlegmator. Any of these may be the principal product of the process. The membrane separation step may also be performed in the vapor phase, or by membrane distillation.

76 Claims, 13 Drawing Sheets

SEPARATION PROCESS USING PERVAPORATION AND DEPHLEGMATION

This invention was made in part with Government support under SBIR awards numbers DE-FG03-98ER82616, awarded by the Department of Energy, and NSF-DMI-0128695 awarded by the National Science Foundation, and in part under a Cooperative Research and Development Agreement (CRADA) between the United States Environmental Protection Agency and Membrane Technology and Research, Inc. The Government has certain rights in this invention.

FIELD OF THE INVENTION

The invention relates principally to the separation of aqueous/organic mixtures by pervaporation. The separation is carried out using a hybrid process combining pervaporation and reflux condensation, also known as dephlegmation.

BACKGROUND OF THE INVENTION

Liquids containing organic compounds and water occur throughout industry.

Such liquids include wastewater streams contaminated with dissolved organic compounds, for example methanol, ethanol or other alcohols, methyl ethyl ketone, other ketones and aldehydes, esters, such as ethyl acetate, phenols, aromatic compounds such as benzene or toluene, and other hydrocarbons, including halogenated hydrocarbons, such as trichloroethane. These organics make the water unfit for reuse or discharge, and are difficult to remove, even at low concentrations.

Other representative liquids include process streams from many chemical processes, such as those conducted in solution, and raw product streams that require purification. Examples within this area include many streams produced by the food industry, such as those that arise during preparation of beverages, such as juices, wine or beer, or when flavors or aromas are extracted. Other examples are streams generated during pharmaceutical production.

Another significant class of processes that yield organic/water containing liquid streams is fermentation. Several important materials, including acetone and ethanol, are made by fermenting corn or other biomass feedstock. Bioethanol is the most important liquid fuel made in the United States from domestically produced renewable resources such as corn and other agricultural crops and food processing wastes.

At present, the U.S. agriculture industry provides approximately 1.3 billion gallons of fuel ethanol per year. Traditional production of bioethanol involves batch fermentation of biomass into alcohol using a biocatalyst, followed by ethanol recovery from the fermentation broth using distillation. The distillation step of this energy-intensive production process accounts for about 40% of the total energy needed for corn-to-ethanol conversion. The high cost of the distillation step has discouraged increased use of this process that is otherwise very attractive to U.S. industry.

Mixtures of organic compounds and water in the vapor phase are also found.

Pervaporation is an energy-efficient membrane-separation process that is used as an alternative to distillation for removal and/or recovery of volatile organic compounds from aqueous solutions and for dehydration of industrial solvents or other organic liquids. The process can provide very selective separation of hydrophobic organic compounds, such as aromatic hydrocarbons or chlorinated solvents, from water, but is much less effective is separating more hydrophilic organics, such as alcohols and ketones.

Membrane distillation is a term sometimes used to describe a distillation process in which the gas and liquid phases are separated by a porous membrane, the pores of which are not wetted by the liquid phase.

Vapor separation is a membrane separation process in which a feed stream that is normally liquid under ambient temperature and pressure conditions is supplied to the feed side of the membrane as a vapor. Thus the process is normally performed at elevated temperatures.

SUMMARY OF THE INVENTION

The invention is a process for separating a liquid containing an organic compound and water, using a combination of pervaporation and reflux condensation, also known as dephlegmation.

The combination process can treat aqueous streams containing one or more dissolved organic compounds, to produce a product stream containing as much as 90 wt % or more organic compound. This high concentration of organic can be achieved even when the organic compound is present at relatively low concentrations in the feed, such as 5 wt % or less, and when the organic compounds are poorly separated from water by conventional organic-selective pervaporation, as is the case with alcohols, for example. In this case, membranes that provide a separation factor in favor of the organic component(s) are preferably used in the pervaporation step to produce an organic-enriched permeate, which is then sent to the dephlegmator for separation by partial condensation. The dephlegmator produces an overhead vapor rich in the more volatile component (usually the organic compound or compounds) and a bottom condensate product rich in the less volatile component (usually the water).

The combination process can also be used to dehydrate organic liquids in which water is dissolved, to yield an organic product containing as little as 1 wt % water or less, and a relatively clean water stream. In this case, dehydration membranes are preferably used in the pervaporation step to produce an organic-enriched residue product stream, from which most of the water has been removed, and a water-enriched permeate. The permeate is sent to the dephlegmator for separation by partial condensation. The dephlegmator produces an overhead vapor rich in the more volatile component (usually the organic compound or compounds, which can optionally be recirculated to the pervaporation step to increase recovery of the organic product), and a bottom condensate product rich in the less volatile component (usually the water).

The process has a number of advantageous features. For example, in a conventional pervaporation process, the permeate vapor is often fully condensed (except for any inert gases that may be present), so that the purity of the product depends entirely on the separation capability of the pervaporation step. Even if partial condensation is used, the vapor and liquid phases leave the heat exchanger together, at equilibrium, so the separation obtained depends only on the vapor/liquid equilibrium ratio at the condensation conditions. In contrast, the present invention uses a dephlegmator, from which the condensate leaves at the bottom and the uncondensed vapor leaves at the top. The dephlegmator tubes, fins or packing elements behave as wetted walls in which the up-flowing vapor and down-flowing condensate are in countercurrent contact. This provides a separation improved, for example, four-fold or six-fold compared with that provided by a simple partial condensation.

Further, only the vapor condensing at the top of the column must be cooled to the lowest temperature. In contrast, a conventional condenser requires all of the vapor to be cooled to the lowest temperature. Therefore, the cooling load required to operate the process of the invention can be significantly less than that required to operate a conventional partial condenser.

The process of the invention involves running a liquid feedstream, containing at least one organic component and water, through a membrane pervaporation system.

The pervaporation system may contain one or more membrane modules, of similar or dissimilar type, and may be arranged in any desired configuration, such as one-stage, multistep or multistage, all of which are known in the membrane separation arts.

The membranes may be chosen to provide an overall pervaporation separation factor in favor of the organic component(s) over water, or a separation factor in favor of water over the organic component(s), and may be of any type capable of operating in pervaporation mode to provide separation between organic components and water. Suitable membranes include, but are not limited to, polymeric membranes and inorganic membranes.

Transport through the membrane is induced by maintaining the vapor pressure on the permeate side of the membrane lower than the vapor pressure of the feed liquid. This is usually, but not necessarily, achieved by operating at below atmospheric pressure on the permeate side. A partial vacuum on the permeate side of the membrane may be obtained simply by relying on the pressure drop that occurs as a result of the cooling and condensation that takes place in the dephlegmator, or may be augmented by use of a vacuum pump. The vapor pressure of the feed liquid may also be raised by heating the feed solution.

The dephlegmator may be of any type capable of providing countercurrent contact between upward flowing vapor and downward flowing condensate, and to provide heat exchange over at least part of the length of the dephlegmator between the feed under treatment and an appropriate coolant. Examples of suitable types of dephlegmator include shell-and-tube and brazed aluminum plate-fin designs, as well as packed columns of various configurations.

The dephlegmation step may be carried out using a single dephlegmator, or may incorporate multiple dephlegmators arranged in series, optionally in such a configuration as to enable multiple products of different compositions to be withdrawn.

The process is useful in diverse circumstances where a solution of organic-in-water or water-in-organic is to be separated. Representative, but non-limiting, application areas are recovery of fermentation products and dehydration of organic liquids. The process may be used, for example, to yield enhanced performance in pervaporation applications, such as those in which the condensed permeate from the pervaporation unit forms a single phase, and/or is not highly enriched in one component, and/or is to be subjected to further treatment, such as distillation.

In some cases, the process of the invention can be used upstream or downstream of a distillation column to unload or simplify the distillation step, or to obviate the need for distillation entirely.

One specific exemplary area in which the process is particularly useful is bioethanol production. By incorporating the process into the production train to provide continuous removal of ethanol, the size of the fermentor can be reduced and the distillation step can be substantially reduced in size or completely eliminated.

Another specific exemplary use is to recover mixed flavor essences from evaporator condensate waters produced when fruit and vegetable juice concentrates are prepared.

In another aspect, other types of membrane separation processes capable of producing a vapor phase aqueous/organic mixture as feed to the dephlegmation step may be substituted for the pervaporation step. Suitable processes include membrane distillation, where the feed to the membrane separation step is in the liquid phase, and vapor separation, where the feed to the membrane separation step is in the gas phase.

Other objects and advantages of the invention will be apparent from the description of the invention to those of ordinary skill in the art.

It is to be understood that the above summary and the following detailed description are intended to explain and illustrate the invention without restricting its scope.

DETAILED DESCRIPTION OF THE INVENTION

Figure 1:
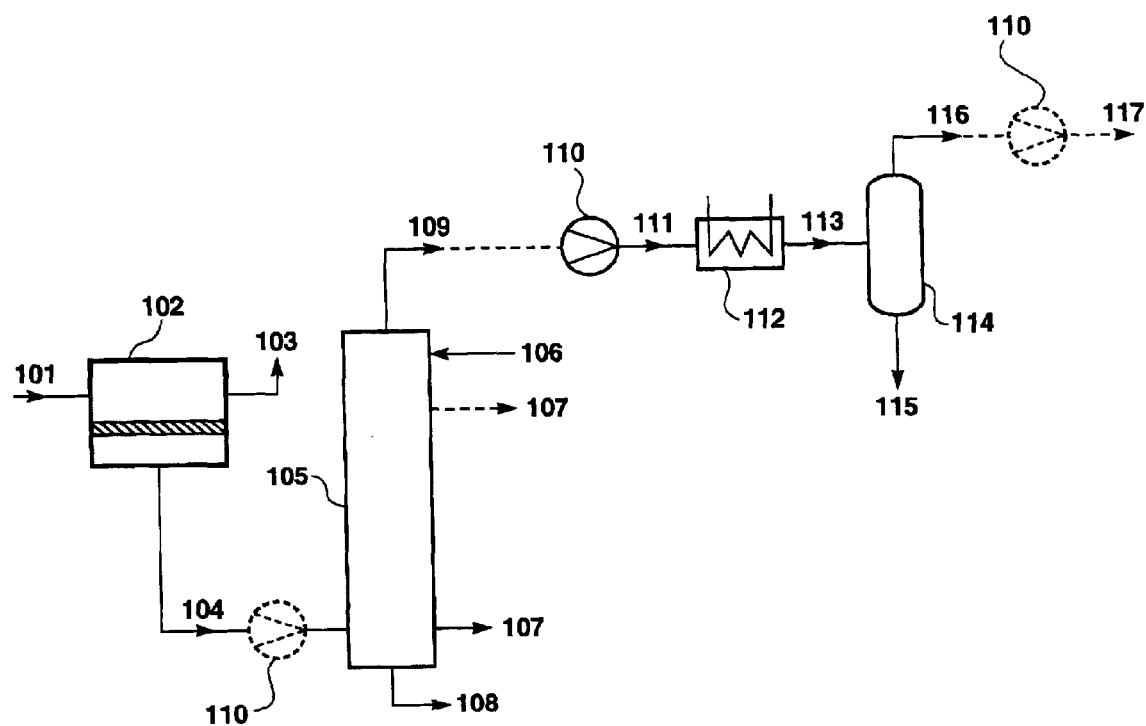
FIG. 1 is a schematic showing a basic embodiment of the invention, optionally including a vacuum pump, condenser and phase separator to collect the overhead product from the dephlegmator.

All percentages herein are by weight unless otherwise stated.

The terms dephlegmation and reflux condensation have the same meaning herein.

The terms vapor and gas are used interchangeably herein.

As used herein, the term dehydration membrane means a membrane that provides an overall pervaporation separation factor in favor of water over organic compounds.

The invention is a process for treating fluids containing organic compounds and water. The fluid may be in the liquid or the gas phase. The invention as it relates to liquid phase feeds is described first.

If the feed to be treated is in the liquid phase, the feed may be water in which one or more organic compounds are dissolved, or an organic liquid in which water is dissolved.

The scope of the invention is not intended to be limited to any particular streams, but to encompass any situation where a stream containing dissolved organic chemicals or containing dissolved water is found. The feed streams that can be treated by the process of the present invention may arise from diverse sources, and include, but are not limited to, industrial wastewaters and other industrial effluents; industrial process streams containing solvents, process reaction products, or the like; contaminated groundwater; product streams and wastewaters from food or beverage processing, containing alcohols, flavor essences or similar materials; and pharmaceutical process waters.

The concentration of the organic components dissolved in the water, or of the water in the organic, if water is the minor component, may be any value, ranging from, for example, ppm levels up to 20 wt %, 30 wt %, 40 wt % or more. In general, however, the process of the invention is especially valuable for recovery of organics from aqueous feeds containing relatively low concentrations of organics, by which we mean feeds containing less than about 20 wt % organics, more preferably less than 15 wt % organics and most preferably less than 10 wt % organics. At these low concentrations, the process is particularly attractive economically compared with other separation technologies.

The process of the invention is also particularly valuable for dehydrating organic liquids containing large amounts of water, such as more than about 10 wt % water, more than about 20 wt % water, more than about 30 wt % water, or higher.

Representative organic materials that may be separated from aqueous solutions by the process of the invention include, but are not limited to, straight-chain, branched, cyclic and aromatic unsubstituted and substituted hydrocarbons, such as decane, toluene or cyclohexane, including hydrocarbon mixtures, such as biodiesel, and oils, such as silicone oil; halogenated compounds, such as perchloroethylene or trichloromethane; esters, such as ethyl acetate or butyl acetate; aldehydes and ketones, such as acetone or methyl ethyl ketone; and alcohols, such as ethanol or iso-propanol.

In general, the more hydrophobic of these materials, such as aromatics and chlorinated solvents, are well separated from aqueous solutions by pervaporation alone. Thus, although the process of the invention can be used satisfactorily to separate these compounds from water, it is especially beneficial in treating feed streams that include organics that are readily miscible with water, such as ketones and alcohols, where separation by pervaporation alone may be more difficult.

Likewise, any organic liquid that contains water may be dehydrated by the process of the invention, although dehydration of alcohols, ketones and the like is particularly attractive from an economic viewpoint.

One specific exemplary area in which the process is particularly useful is in the manufacture of organic products by fermentation performed in batch or continuous mode. Fermentation is currently used to make acetone, ethanol, isopropanol, n-propanol, n-butanol, amyl alcohol, acetic acid, other organic acids and flavor compounds, for example.

A major example of such manufacturing is the production of ethanol from corn or other biomass. In the interests of clarity and simplicity, therefore, our process is described herein principally as it relates to ethanol/water separation. However, this is intended to avoid long and complicated lists of equivalents whenever process streams are discussed, and is not intended to limit the scope of the process. Those of skill in the art will readily appreciate how to apply the process of the invention to other organic/water and water/organic mixtures by following the exemplary teachings specific to ethanol/water that are given herein.

Also, although the description refers principally to ethanol/water separation, this should not be construed to mean that only streams containing a single organic component and water can be treated. Indeed, in bioethanol production, the fermentation broth will usually contain multiple organic components, such as other alcohols and ketones, as in the ABE (acetone-butanol-ethanol) fermentation process, that will be separated with the ethanol from the water.

Another good example of an area in which the process can be used to separate multiple organic components from water is in the food, flavor and fragrance industries. For instance, in the production of fruit and vegetable juice concentrates, fresh filtered juice is concentrated four or five times in multiple-effect evaporators. As well as removing water, the evaporation step removes a considerable fraction of the volatile aldehydes, alcohols and esters that constitute the characteristic flavor profile of the juice. Most of these components are removed in the first evaporator effect. The process of the invention can treat this condensate to recover flavor components as a high-value concentrated oil product, or to be returned to the juice.

The invention includes two unit operations—membrane separation and dephlegmation. The membrane separation step is generally performed first, and the membrane permeate is sent to the dephlegmator.

Several membrane separation operations are capable of treating a feed liquid containing organic components and water to produce a permeate in the form of a vapor comprising an organic/water mixture of a different composition.

Pervaporation is a low-pressure membrane process that can be used to separate components of differing volatilities from solutions. The overall separation factor achieved is equal to the product of the separation achieved by evaporation of the liquid and the separation achieved by selective permeation through the membrane. The membranes for use in the process of the invention may be of any kind that results in an overall separation factor in favor of organics over water, or in favor of water over organics. It is preferable, but not necessary, to use a membrane that will result in an overall separation factor in favor of the minor component. Thus, if the mixture to be separated contains, say, 10 wt % acetone in water, it is preferred to use a membrane that provides a separation factor in favor of acetone over water; if the mixture to be separated contains, say, 10 wt % water in acetone, it is preferred to use a dehydration membrane.

A number of materials offer pervaporation separation factors in favor of organic compounds over water. Preferred membrane materials of this type include rubbery non-crystalline polymers, with glass transition temperatures below the normal operating temperature of the system. Thermoplastic elastomers are also useful. These polymers combine hard and soft segments or domains in the polymer structure. Provided the soft segments are rubbery at the temperature and operating conditions of the invention, polymers of this type could make suitable membranes for use in the invention. Polymers that may be used include, but are not limited to, nitrile rubber, neoprene, polydimethylsiloxane (silicone rubber), chlorosulfonated polyethylene, polysilicone-carbonate copolymers, fluoroelastomers, plasticized polyvinylchloride, polyurethane, cis-polybutadiene, cis-polyisoprene, polychloroprene, poly(butene-1), ethylene-propylene copolymers and terpolymers, polystyrene-butadiene copolymers, styrene/butadiene/styrene block copolymers, styrene/ethylene/butylene block copolymers, thermoplastic polyolefin elastomers, polyesteramides, and block copolymers of polyethers and polyesters.

The most preferred rubbery polymer membrane material is silicone rubber.

Another type of membrane that has been reported to provide good pervaporation separation factors for organics over water, indeed much higher than silicone rubber, at least in favor of ethanol over water, is a rubbery membrane impregnated with small hydrophobic zeolite particles, such as silicalite particles. Such membranes are described in U.S. Pat. No. 4,925,562, assigned to GFT Gesellschaft fur Trenntechnik mbH, and are now offered commercially by Sulzer Chemtech, of Winterthur, Switzerland.

Yet another type of preferentially organic permeating membrane that can be used is an entirely inorganic membrane, such as a tubular membrane comprising a hydrophobic zeolite layer or particles. Such membranes are described, for example, in J. Caro et al., "Zeolite membranes—state of their development and perspective", *Microporous and Mesoporous Materials*, Vol. 38, 3–24, 2000.

For use as dehydration membranes, a number of suitable materials are also known. Polyvinyl alcohol (PVA) is the most commonly used commercial material. Another polymer that has sometimes been used is cellulose acetate. Yet other suitable membrane include chitosan membranes and ion-exchange membranes, such as Nafion® membranes.

Inorganic membranes comprising hydrophilic materials may also be used as dehydration membranes. Such membranes include amorphous silica membranes and membranes including a water permeating zeolite layer, such as ZSM-5. Such membranes are also discussed in the Caro et al. paper above, and have been developed commercially, for example, by the Mitsui and Company of Japan.

Various types of inorganic membranes may be purchased from Mitsui and Company (USA) of New York, Isotronics of Paradise Valley, Ariz., Sulzer Chemtech Membrane Systems, based in Heinitz, Germany, and Pervatech BV of Enter, Netherlands.

The membrane may take the form of a homogeneous membrane, an asymmetric membrane, a multilayer composite membrane, a matrix incorporating a gel or liquid layer, or any other form known in the art. If the membranes are polymeric membranes, a particularly preferred form is a composite membrane, comprising at least a microporous, relatively unselective support layer and a thin selective coating layer, and optionally other layers, such as a backing, a gutter layer, and a sealing or protective top layer. The making of such membranes is well known in the art.

The membranes may be formed as flat sheets, hollow fibers, tubular membranes or any other convenient form, and housed in any appropriate cartridge or module configuration, such as a spiral-wound module, a plate-and-frame module or a potted hollow-fiber cartridge. In a preferred embodiment for polymeric membranes, the membranes are cast and coated as flat sheets, and then rolled into spiral-wound modules. The preparation of spiral-wound modules is well known in the art. A preferred form for inorganic membranes is a ceramic tubular module, as is well known in the art.

The pervaporation unit can include a single membrane module or a bank or array of multiple membrane modules. A single bank of membrane modules is usually adequate to meet the processing requirements for many applications. If additional processing is desirable, an array of modules in a multistep or multistage configuration with recycle of intermediate streams, as is known in the art, may be used. For example, if the residue stream requires further purification, it may be passed to a second bank of membrane modules for a second processing step. Such an arrangement may be useful if the feed stream contains a relatively high concentration of organics in water, for example, and the residue water stream must be reduced to a very low organic content to meet discharge specifications.

If multiple membrane modules are used, the individual modules or banks of modules may provide like or unlike separation factors. For example, a first stage providing an organic-enriched permeate may be followed by a second stage providing a water-enriched permeate.

A second type of membrane separation operation capable of treating a feed liquid containing organic(s) and water and producing a vapor permeate is membrane distillation. Membrane distillation provides a separation based on the vapor-liquid equilibrium of the components to be separated under the prevailing conditions of temperature and pressure.

A porous membrane is used to separate the liquid and vapor phases, and a sweep gas or vapor, such as nitrogen, may be used on the permeate side. In membrane distillation, the membrane should be of a material that is not wetted by the feed liquid. Suitable membranes for use in the present invention include Celgard® polypropylene membranes, available from Celgard Inc, of Charlotte, N.C., and Teflon®, that is, polytetrafluoroethylene (PTFE) membranes, such as those available from Compact Membrane Systems, of Wilmington, Del.

Since separation depends on the vapor-liquid equilibrium at the prevailing conditions, the feed may be supplied to the membrane at warmer than ambient temperatures. In addition, or alternatively, a sweep gas, such as nitrogen, may be used on the permeate side to remove the permeating vapor continuously. Such a process offers benefits in removing thermally labile flavor compounds from water, for example. In this case, the feed may be provided to the membrane without heating, and nitrogen used as a sweep gas to carry away the permeating flavor elements from the permeate side.

For simplicity, the description of FIG. 1 that follows refers to the embodiments of the invention in which the membrane separation step is pervaporation. However, it will be appreciated by those of skill in the art that FIG. 1 also applies to embodiments in which the membrane separation step is carried out by membrane distillation, the difference being that element 102 of the flow scheme is then a membrane distillation step.

Referring now to FIG. 1, feed stream, 101, containing an organic compound and water, is introduced into pervaporation step or unit 102. The pervaporation unit used in this step is equipped with an array of one or more membrane modules. Ethanol (or other organic component) and water pass through the membrane as vapors. If the membrane separation factor favors ethanol, the ethanol permeates faster than the water; if the membrane separation factor favors water, the water permeates faster than the ethanol.

The non-permeating portion of the feed stream is removed as a liquid residue stream, 103.

If the membrane provides a separation factor in favor of ethanol, stream 103 will be depleted in ethanol and enriched in water compared with the feed solution. Stream 103 can pass to any destination. For example, it may be discharged as waste, returned to the originating process, directed to another process, or recycled in part or in whole in a loop around the pervaporation step.

If stream 103 is to be directly discharged, then the pervaporation process should remove a sufficient amount of the ethanol so that stream 103 meets permitted levels. Although permitted levels are location specific, the pervaporation process will most likely be required to remove at least 80% of the organic content in this case. Thus, if the feed contains, for example, 10 wt % ethanol, it may be desired to adjust the membrane area and operating parameters such that the residue stream contains no more than about 1 wt % ethanol, for example.

If stream 101 originates from a fermentor and if the purpose of the pervaporation process is to reduce fermentation inhibition caused by the ethanol, then stream 103 will typically be returned to the fermentor vessel(s). In this case, the membrane separation step acts as a selective bleed, and the fraction of ethanol removed by the pervaporation process in a single pass will likely be substantially less than 80%, and more typically just a few percent, for example 5%. Other possible destinations if the feed originates from a fermentation operation include the beer well, in a facility so equipped, and the process water supply. The exact fraction of ethanol to be removed by the pervaporation stage will depend on economic and regulatory constraints for a particular situation but will, therefore, likely be in the range of 5 to 95% removal.

If the membranes preferentially permeate water, stream 103 will be depleted in water and enriched in organic component(s) compared with the feed solution. In this case, stream 103 may be the primary product stream of the process. For example, if the membrane is used to dehydrate 95 wt % ethanol containing 5 wt % water, stream 103 should preferably have a composition of at least about 99 wt % ethanol, and most preferably at least about 99.5 wt % ethanol.

Transport through the membrane is induced by maintaining the vapor pressure on the permeate side of the membrane lower than the vapor pressure of the feed liquid. On the feed side of the membrane, the partial vapor pressure of any component will be the partial pressure of the vapor in equilibrium with the feed solution. Changing the hydrostatic pressure of the feed solution thus has a negligible effect on transmembrane flux or selectivity.

However, the vapor pressure on the feed side is a function of the temperature of the feed solution. Optionally, therefore, the feed may be heated before it is passed to the pervaporation unit. Again using the recovery of products from an aqueous fermentation solution by way of illustration, two non-limiting examples may be given. In the case that the process is used to bleed alcohols or other products from the fermentation broth, with the membrane residue stream being returned to the reactor, the feed should be heated only moderately, if at all, to a temperature no more than about 30° C., 40° C. or 50° C., depending on the specific type of fermentation being used, so as not to damage or kill the fermentation organisms.

On the other hand, if the process is used to handle a stream, such as an aqueous waste stream, where preservation of thermally sensitive materials is not a concern, the feed may be heated to a relatively high temperature, such as 50° C., 60° C. or even higher, to increase driving force, and hence permeation rate, in the pervaporation step.

Although changing the hydrostatic pressure on the feed side has little effect, changing the permeate pressure has a major effect on transmembrane flux. The vapor pressure of a component on the permeate side can be reduced in several ways, for example, by drawing a vacuum on the permeate side of the membrane, by sweeping the permeate side to continuously remove permeating vapor, or by cooling the permeate vapor stream to induce condensation.

In the present invention, the permeate will be partially condensed in the reflux condensation step, and this generates a partial vacuum on the permeate side. If specific circumstances (such as the properties of the organic components to be separated from the water, energy considerations, or a desire to avoid equipment that requires maintenance) so indicate, it is possible to operate the process in this way without the use of a vacuum pump. Optionally, a greater transmembrane driving force, and hence higher flux and greater separation, may be as achieved by further reducing the pressure on the permeate side by means of a vacuum pump. This may be done by positioning a vacuum pump, 110, in the overhead line from the dephlegmator, as shown in FIG. 1, or in the permeate line, 104.

Of course, if the vacuum pump is positioned as shown by the solid element 110 in the figure, this will also create a partial vacuum in the dephlegmator. Pressure considerations for the dephlegmation step are discussed below.

If the process taking place in step 102 is not pervaporation but membrane distillation as described above, a vacuum pump is positioned in line 116 before or after the phase separator to remove sweep gas, which may then be recirculated to the permeate side of the membrane distillation step. Although a vacuum pump may also be positioned in line 104, it is generally adequate to pass the sweep gas at atmospheric pressure on the permeate side, and to use a simple blower to pass gas from the membranes to the dephlegmator.

Returning to the general pervaporation-based description of the embodiment of FIG. 1, permeate stream 104 is in the vapor phase, and comprises an organic/water mixture of a different composition than feed stream 101. Since it is preferred to use a membrane that provides an overall separation factor in favor of the minor component(s) of the feed stream, the permeate vapor will usually be enriched in this minor component(s) and depleted in the other component.

For example, using the ethanol dehydration illustration above, the permeate vapor stream will be enriched in water. Dehydration membranes tend to offer relatively high separation factors for water over ethanol, such as 100 or more. Therefore, even if the feed contains only one or two percent water, the permeate will typically be highly enriched in water, and may often contain 30 wt % water, 40 wt % water, 50 wt % water or even more. With a less-selective membrane, the permeate stream will be less enriched.

If ethanol is the minor component, the separation factor for ethanol over water provided by the membranes is likely to be lower, typically in the range between 5 and 20, such as about 10 or less. In this case, the enrichment obtained in the permeate vapor stream 104 is likely to be no more than about 5- or 10-fold. Thus, if the ethanol concentration in the feed solution is 2 wt %, the concentration in the permeate is usually in the range 15–20 wt %, and if the ethanol concentration in the feed solution is 5 wt %, the concentration in the permeate is usually in the range 35–40 wt %.

With a more hydrophobic organic compound, such as acetone, for example, a higher organic/water separation factor, such as 50 or above, is possible, in which case the permeate will be richer in the organic component. In this case, even if the feed contains only 1 wt % acetone, for example, the permeate vapor stream 104 may contain 30 wt %, 40 wt % or more acetone.

The invention also includes processes in which the pervaporation step is performed using a membrane that provides a separation factor in favor of the major component of the feed stream. In this case, the permeate vapor will be yet richer in the major component. For example, if a membrane providing a separation factor in favor of water is used to treat a feed containing isopropanol (IPA) and water in equal amounts, or containing more than 50 wt % water, the permeate vapor will be very water-rich, containing as much as 90 wt % water or 95 wt % water, for example.

Stream 104 is introduced as a feed stream into dephlegmation step or unit 105, at or near the bottom of the unit, as shown in FIG. 1. A coolant stream, 106, is introduced at or near the top of the dephlegmator column as shown in FIG. 1 and flows down a coolant channel or channels that are in heat-exchanging relationship with the channels carrying the upward-flowing feed stream 104.

As mentioned above, the dephlegmator may be of any type capable of providing countercurrent contact and mass transfer between upward-flowing vapor and downward-flowing condensate, and to provide heat exchange as described in the previous paragraph over at least part of the length of the dephlegmator column.

A non-limiting example of a type of dephlegmator that may be used for the process of the invention is a vertical shell-and-tube arrangement in which the cooling medium flows on the shell side and the feed vapor is introduced into the tube bores. Another example of a suitable type is a vertical brazed aluminum plate-fin design. Similar units are known and used as conventional heat exchangers throughout the chemical engineering industry. They have also been used as dephlegmators to improve the performance of cryogenic distillation columns for gas separation in refineries and petrochemical plants.

Yet other examples of suitable configurations are columns containing a structured packing that provides for a high surface area of contact between rising vapor and falling condensate. Such a dephlegmator may take the form of a column with an interior volume or volumes of large dimensions containing the structured packing material in a manner similar to that used in a stripping tower. Alternatively, the dephlegmator may take the form of a shell-and-tube heat exchanger, with the structured packing held within the feed-flow channels. Such a configuration gives a very high contact area for heat and mass transfer between vapor and condensate.

The dephlegmator should provide a high heat transfer area per unit volume, such as at least about 100 $m^2/m^3$. In general, shell-and tube dephlegmators offer heat-exchange densities between about 80 and 300 $m^2/m^3$. If packing is used, this can be increased to about 1,000 $m^2/m^3$. Plate-fin dephlegmators tend to have higher heat-exchange densities, between about 800 and 1,500 $m^2/m^3$.

FIG. 1 shows the coolant stream exiting the column at the bottom as stream 107. Thus, in this case, external cooling is provided over the length of the column. As an alternative, it is possible to provide external cooling only in the upper portion of the column, and to rely on the cool falling condensate to simultaneously provide both heat and mass transfer with the warm rising vapor in the lower portions of the column. In this case, stream 107 will be withdrawn higher up the column at the desired point, as indicated by the dashed line in FIG. 1.

Such an arrangement may incorporate more than one type of dephlegmation configuration. For example, the upper part of the dephlegmator, where most cooling is required and through which the external coolant is passed, may be of the shell-and-tube or plate-fin design, and the lower part, where heat exchange takes place directly between up-flowing vapor and down-flowing condensate, may take the form of a packed column. More complicated vertical "stacks" including three or more styles of dephlegmation operation are also possible.

The coolant may simply be cold water, or may be a refrigerant that cools the vapor to a lower temperature, such as 0° C. or below. The cooling or refrigeration step uses less energy than the comparable cooling or refrigeration step in a simple partial condensation operation. The reason is that only the portion of vapor condensing at the top of the column must be chilled to the lowest temperature. At least some of the cooling duty is performed by the condensate itself as it travels down the column. In contrast, a simple partial condenser has to cool the entirety of the vapor stream to the condensation temperature.

When the process is in operation, warm membrane permeate vapor passes into the column as stream 104 as shown and rises in the feed passages or channels. A portion of the vapor condenses on the comparatively cold tube or channel walls or packing surfaces; this condensate runs downward within the feed passages, countercurrent to the feed vapor. Mass transfer between the condensate liquid and the vapor enriches the liquid in the less volatile component or components and the vapor in the more volatile component or components.

The liquid condensate, enriched in the less volatile component, exits the dephlegmation step as bottom product stream 108. The vapor stream, enriched in the more volatile component, exits the dephlegmation step as overhead product stream 109. It is also possible to withdraw an intermediate product or products as side streams of different compositions at points along the height of the column.

Depending on their relative volatilities, the more volatile component enriched in the overhead product may be either the organic component(s) or water. Many of the separation applications for which the process of the invention is suited involve the separation from water of organics of lower boiling point and higher volatility than water. For example, in the separation of fermentation products such as common alcohols or acetone, the alcohol or acetone components will be concentrated in the overhead stream and water will be concentrated in the bottom stream.

However, organic/water mixtures in which the organic component(s) are less volatile than water are also commonly encountered. Specific streams of this type that can be handled well by the process of the invention include, but are not limited to, solutions of phenols and water, solutions of acetic acid and water, solutions of biodiesel and water and solutions of silicone oil and water.

For example, if a feed solution containing a few percent phenol in water is to be treated, a pervaporation membrane (such as a polyamide-polyether block copolymer membrane) that provides a separation factor in favor of phenol may be used to obtain a phenol-enriched permeate vapor. In the dephlegmation step that follows, this permeate vapor is separated into a condensed phenol-rich bottoms product and a water-rich overhead vapor.

Similarly, if a feed solution of acetic acid containing about 10 wt % or 20 wt % water is to be treated, a dehydration pervaporation membrane (such as a PVA or ceramic membrane) may be used to obtain a water-enriched permeate vapor. In the dephlegmation step that follows, this permeate vapor is separated into a condensed acetic-acid-rich bottoms product and a water-rich overhead vapor.

Variables that affect the performance achieved by the dephlegmator include the coolant temperature, coolant flow rate, composition and temperature of the entering feed vapor, vapor feed rate, and pressure within the dephlegmator. In general, the lower is the temperature of the overhead vapor product stream 109 from the dephlegmator, the higher is the concentration of the more volatile component in that overhead product. A lower overhead product temperature may be achieved by increasing the coolant flow rate, or lowering the coolant temperature, or both.

Also in general, the higher is the temperature of the bottoms condensate product stream 108, the greater is the recovery of the more volatile component in the overhead product stream. A higher bottom product temperature may be achieved by raising the coolant temperature, or lowering the coolant flow rate, or both.

Since a driving force for membrane permeation is provided in the membrane separation step 102 by a vapor pressure difference between the feed and permeate sides, it is optional to draw a partial vacuum on the permeate side to enhance flux of the permeating components through the membrane, as mentioned above.

If this is done by positioning vacuum pump 110 as shown by the solid element 110 in FIG. 1, the dephlegmation step will also be operating under the same degree of vacuum. However, a more desirable option may be to operate the dephlegmator at a higher absolute pressure than the pervaporation module. The higher pressure in the dephlegmator allows the use of a higher coolant temperature and should also increase column throughput, both of which will be more cost-effective, all other parameters being equal. This higher pressure can optionally be achieved by placing the dephlegmator after a blower or vacuum pump positioned in line 104, as shown by the dashed element 110 in that line. The advantages of a higher dephlegmator pressure can also be achieved by operating the pervaporation stage at a higher absolute pressure, although this can reduce the performance of the pervaporation stage.

Yet another option is to position a vacuum pump 110 after a condenser/phase separator in the overhead line, as shown by the dashed element 110 in line 116, either before the phase separator (shown) or after the phase separator (not shown). In this case, both the permeate pressure for the pervaporation step and the operating pressure of the dephlegmation step are controlled not by pump 110, which is now a much smaller pump used to evacuate non-condensable components such as air that may be present in the overhead, but rather are set by the operating temperature of condenser 114. The operation of the elements 111–117 in this case is discussed in more detail below.

Depending on the specific economic considerations and technical requirements, one of ordinary skill in the art will be able to select the pump position and capacity most appropriate for any particular separation. In some circumstances, a pump or blower in line 104 may be used in addition to a small pump to vent non-condensables in line 116, for example.

Representative data showing the effects of changing significant operating variables are given in the Examples section below for the separation of ethanol from water. It will be apparent to those of skill in the art that these operating temperatures, pressures, flow rates and so on are merely illustrative and should not be construed as limits, either for ethanol/water separations, or for separation from water of other organic compounds of substantially different physical properties.

Theoretical treatments on the basis of which suitable operating parameters for a specific separation may be calculated by the skilled person are found, for example, in (i) S. Di Cave et al., "Mathematical Model for Process Design and Simulation of Dephlegmators (Partial Condensers) for Binary Mixtures", *Canadian Journal of Chemical Engineering*, Vol. 65, 559–564, 1987; (ii) R. J. Jibb et al., "The Potential for Using Heat Transfer Enhancement in Vent and Reflux Condensers", (available from web site of Cal Galvin Ltd. at http://www.calgavin.co.uk/news); and (iii) G. A. Lucadamo et al., "Improved ethylene and LPG recovery through dephlegmator technology", *Gas Separation and Purification*, Vol. 1, 94–102, 1987.

The dephlegmation step offers a much higher degree of separation between components than is usually achieved by partial condensation in a simple condenser. In a simple condenser, the vapor and liquid phases leave the heat exchange section together and, therefore, at equilibrium under the prevailing pressure and temperature conditions, so that only a single-stage separation is obtained. In a dephlegmator, the two phases leave at opposite ends, at different temperatures, and the separation obtained is equivalent to multiple separation stages. As is shown in the Examples section below, a dephlegmator of modest physical dimensions operated under conditions of modest energy expenditure with cool water or glycol as coolant and a small temperature difference between overhead and bottoms stream can provide a good separation equivalent to four, six or more theoretical separation stages.

In the case of the separation of ethanol from water, the overhead vapor stream 109 forms the enriched ethanol product of the dephlegmation step. Typically, but not necessarily, this vapor will contain at least about 90 wt % ethanol.

A simple, optional, way to recover this product is shown in FIG. 1. The overhead stream 109 enters vacuum pump 110 on the suction side and emerges at higher pressure as exhaust stream 111. This stream is then subjected to simple condensation by passing through heat exchange step 112, emerges as two-phase mixture 113 and is collected as liquid stream 115 from phase separator 114. Any non-condensed gases remaining are removed as stream 116.

As was mentioned in the discussion of pump placement options above, an alternative arrangement is to position the vacuum pump after the condensation/phase separation step, in line 116 as shown by the dashed pump element 110. This has advantages in that the pump can be of small capacity, since it has only to process any non-condensed gas, rather than the entire overhead stream. On the other hand, the condensation step then takes place on the low pressure, rather than exhaust, side of this pump.

In this arrangement, overhead stream 109 passes without pressure change as stream 111 to heat exchange step 112, emerges as two-phase mixture 113, and is again collected as liquid stream 115 from phase separator 114. Any non-condensed gases remaining are removed under suction as stream 116, pass through vacuum pump 110 and are vented from the process as stream 117. A portion of the condensate stream 115 may be recirculated at the top of the column as a reflux stream if desired.

Another non-limiting option is to further purify stream 109 by submitting it to distillation. In this case, the dephlegmation step is valuable in improving the concentration and reducing the volume of the stream to be distilled. Additional options for stream 109 are mentioned below.

Yet another non-limiting option is to recirculate stream 109 to the inlet of membrane separation step 102 for further processing. This option is useful, for example, in the case that a dehydration membrane is used for step 102, in which case the overhead stream 109 may be less concentrated in ethanol than the membrane residue stream 103. For such configurations, stream 103 is the purified organic product stream, and stream 109 becomes an internal process stream, not a product stream.

Condensate bottoms streams 108 may also be an internal process stream or a product stream. This stream is depleted in ethanol compared with stream 104, and may typically contain a few percent ethanol, such as up to about 10 wt % ethanol.

If membrane separation step 102 uses a membrane that provides a separation factor in favor of organics over water, stream 103 is likely to be the most water-rich, ethanol-lean stream of the process. Thus, the water leaves the process via this stream. By way of non-limiting example, stream 103 may contain less than 1 wt % ethanol, and stream 108 may contain about 5 wt % ethanol. A non-limiting option in this case is to recirculate stream 108 to the inlet of membrane separation step 102 for further processing, so that stream 108 forms an internal process stream.

On the other hand, if membrane separation step 102 uses a dehydration membrane, stream 103 is ethanol rich, and stream 108 is the most water-rich stream of the process. In this case, water exits the process by discharging stream 108 from the process to any external destination. As one non-limiting destination option, if stream 101 arises from bioethanol production, and stream 108 contains only very small amounts of ethanol, stream 108 may be returned to the fermentor.

The process of the invention has been described so far as it incorporates a dephlegmation step carried out as a single operation in one dephlegmator column. As will be appreciated by those of skill in the art, the dephlegmation step may also be performed in multiple sub-steps, using two or more dephlegmator columns of similar or dissimilar configuration in series. The vertically stacked dephlegmation sections discussed above may be considered in some regards as such multiple sub-steps.

However, an arrangement of a series of discrete dephlegmation columns is also within the scope of the invention. In this case, the overhead vapor or a portion of the overhead vapor from one column forms the feed to the next. Such an arrangement is useful, for example, to handle a feed consisting of an aqueous solution in which several organic components of lower volatility than water are dissolved. By adjusting the operating parameters for each column individually, it is possible to recover discrete organic products of different composition as the bottoms streams from individual columns. For example, a juice evaporator condensate may be processed using a flow scheme of this sort to recover several essence fractions separately.

The process of the invention is well suited to be used in conjunction with other separation treatments either upstream or downstream. For example, process feed stream 101 may originate as a stream from another separation process, such as absorption, adsorption, solvent extraction, stripping, scrubbing, condensation, evaporation, distillation, or another pervaporation process.

In like manner, there is no restriction on the destination of streams 103, 108 and 109, any of which may be further separated by means of additional pervaporation or dephlegmation treatment, or by distillation, condensation, phase separation, evaporation, stripping, scrubbing, absorption, adsorption or the like.

So far, the process of the invention has been described as it relates to the treatment of liquid-phase feed streams. It is also possible to treat feed streams that are in the gas phase. Such feeds may arise because the process generating the feed is itself performed in the gas phase, or maybe prepared by boiling a liquid feed to vaporize all or part of the stream before it is introduced into the process.

Since water is a component of the stream to be separated, the temperature of such a stream will generally be above 100° C. (unless the feed is at subatmospheric pressure), and may be considerably higher, such as 150° C., 200° C. or more. The membranes used to perform the separation should, therefore, be able to withstand relatively high temperatures. For the lower end of the temperature range, polymeric materials as listed above may be used. Few currently available polymer membranes can be operated at temperatures above about 150° C., however, so for temperatures higher than this, inorganic membranes such as those described above should be used.

Vapor phase membrane separation, like pervaporation, is a pressure-driven process, that is, transport through the membrane is induced by maintaining the vapor pressure on the permeate side of the membrane lower than the vapor pressure of the feed liquid. If the feed is an ethanol/water mixture at 125° C., for example, the vapor pressure will be in the range about 2–5 atm, depending on the composition. If the feed vapor is at 150° C., the vapor pressure will be in the range about 5–10 atm, and if the feed temperature is 220° C., the vapor pressure will be in the range about 25–60 atm.

In many cases, maintaining the permeate side of the membrane at atmospheric pressure, will, therefore, provide adequate transmembrane driving force. If a greater vapor pressure difference is required, this may be obtained by operating under partial vacuum in similar manner to that described above with respect to pervaporation applications, or by sweeping the permeate side of the membrane with gas or steam, in similar manner to that described above with respect to membrane distillation applications.

The process of the invention in this aspect is also illustrated by the flow scheme of FIG. 1. In this case the vapor feed enters the process as stream 101 and passes through vapor separation step 102, which can be equipped with water-selective or organic-selective membranes of the same types as discussed above. Non-permeating vapor is withdrawn as stream 104. Permeate vapor stream 104 passes to the dephlegmation step, which is carried out generally as described with respect to the pervaporation embodiment above. In this case, it is preferred to maintain the permeate side of the membrane at atmospheric pressure, to pass permeate vapor to the dephlegmator by means of a simple blower and to position pump 110 in line 116 to remove any non-condensable gases.

The invention is now further described by the following examples, which are intended to be illustrative of the invention, but are not intended to limit the scope or underlying principles in any way.

EXAMPLES
SET I—Pervaporation Experiments

Example 1

Membrane and Module Preparation

Two types of composite membranes were prepared by standard casting and coating techniques. A silicone rubber (polydimethylsiloxane) selective layer was coated onto a polysulfone support membrane. A styrene-butylene/ethylene block copolymer (Kraton® Polymers) selective layer was coated onto a silicone rubber gutter layer on a polysulfone support membrane. The resulting composite membranes had a selective layer 0.8–1.5 μm thick. The composite membranes were rolled into 2×12-inch and 4×36-inch spiral-wound modules as are known in the art. The 2-inch module contained approximately 0.2 m² of membrane area; the 4-inch module contained approximately 4.5 m² of membrane area.

Example 2

Water-Ethanol Separations

The 2-inch spiral-wound membrane modules were tested in a pervaporation test system with water-ethanol solutions. A small pump was used to circulate the solutions through the test module. A vacuum pump was used to produce the low pressure required on the permeate side of the membrane, and a permeate condenser system collected the liquified permeate vapor. During the tests, feed and permeate samples were withdrawn for analysis by gas chromatography (GC) or high-pressure liquid chromatography (HPLC). The ethanol concentrations were varied from 0 to 95 wt %, the temperature was varied from 20 to 50° C., and the permeate pressure was varied from 5 to 60 mmHg. The fluxes were measured and the pervaporation separation factors were calculated. The results are shown in Table 1.

TABLE 1

| Membrane | Average Ethanol Flux (L/m² · h) | Ethanol/Water Separation Factor |
|---|---|---|
| Silicone Rubber | 2.1 | 2–15 |
| Kraton ® Elastomer | 0.4 | 4–6 |

Example 3

Water-1,1,2-Trichloroethane Separations

The experiment of Example 2 was repeated with water-1,1,2-trichloroethane solutions. The 1,1,2-trichloroethane concentrations were varied from 0 to 0.1 wt %, the temperature was varied from 30 to 50° C., and the permeate pressure was varied from 5 to 20 mmHg. The fluxes were measured and the pervaporation separation factors were calculated. The results are shown in Table 2.

TABLE 2

| Membrane | Average 1,1,2-Trichloroethane Flux (L/m² · h) | 1,1,2-Trichloroethane/ Water Separation Factor |
|---|---|---|
| Silicone Rubber | 1.5 | 10–35 |
| Kraton ® Elastomer | 0.4 | 90–170 |

Example 4

Water-Methanol Separations

The experiment of Example 2 was repeated with water-methanol solutions with the silicone rubber membrane only. The methanol concentrations were varied from 0 to 95 wt %, the temperature was 30° C., and the permeate pressure was 20 mmHg. The average methanol flux was 5.0 L/m² h, and the calculated pervaporation separation factors were in the range 1–12.

Example 5

Water-Propanol Separations

The experiment of Example 2 was repeated with water-propanol solutions with the silicone rubber membrane only. The propanol concentrations were varied from 0 to 90 wt %, the temperature was 30° C., and the permeate pressure was 20 mmHg. The average propanol flux was 5.5 L/m² h, and the calculated pervaporation separation factors were in the range 1–10.

Example 6

Water-Acetone Separations

The experiment of Example 2 was repeated with water-acetone solutions with the silicone rubber membrane only. The acetone concentrations were varied from 0 to 10 wt %, the temperature was 30° C., and the permeate pressure was 20 mmHg. The average acetone flux was 3.5 L/m² h, and the calculated pervaporation separation factors were in the range 30–50.

As can be seen from Examples 2–6, the membranes had a smaller separation factor for the less volatile, more-water-miscible organics, such as ethanol and acetone, and a larger separation factor for the more volatile, less-water-miscible organics, such as 1,1,2-trichloroethane.

Example 7

Figure 2:
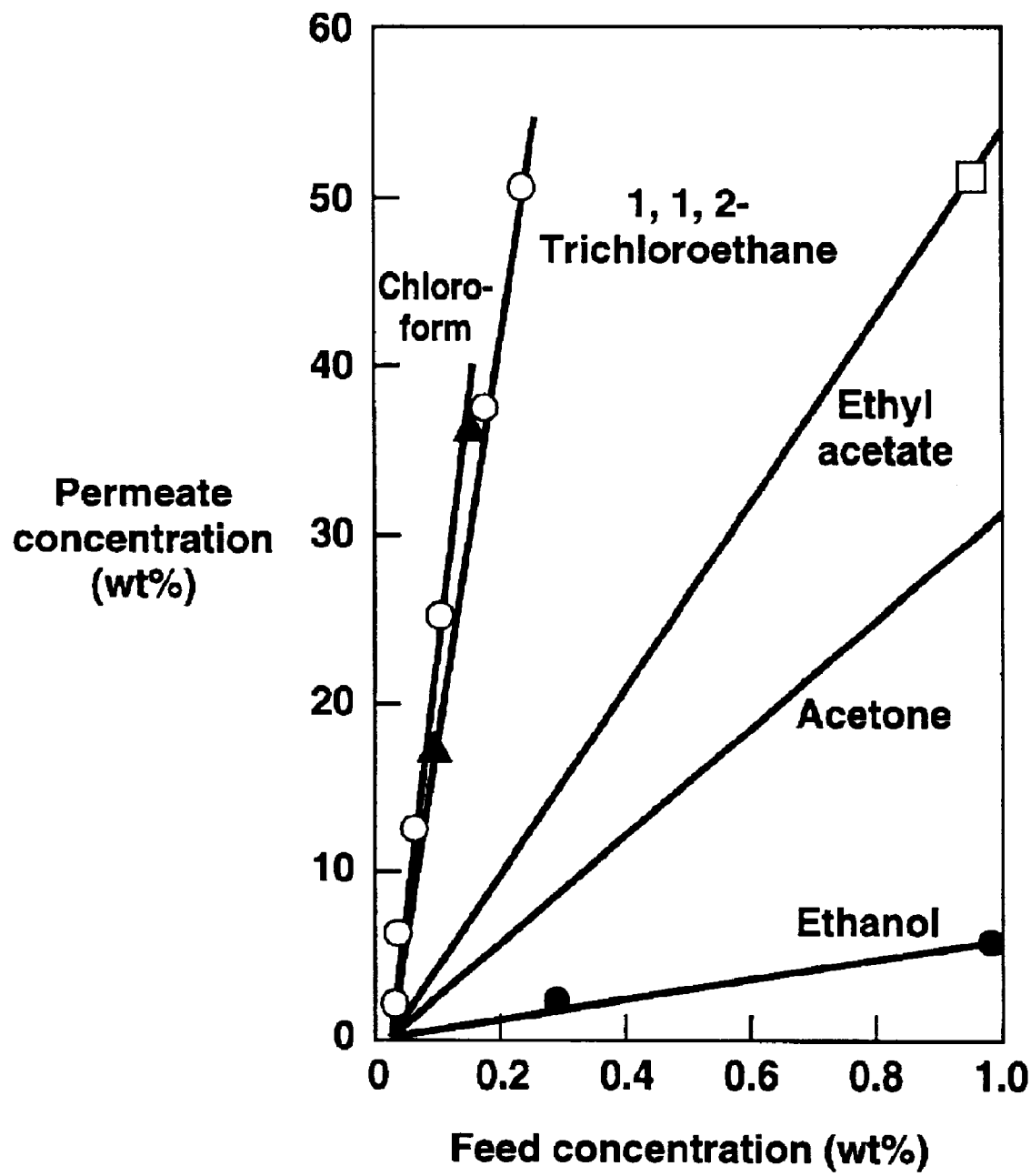
FIG. 2 is a graph of permeate concentration versus feed concentration for pervaporation experiments performed with aqueous solutions containing various organic compounds at concentrations up to 1 wt %.
Figure 3:
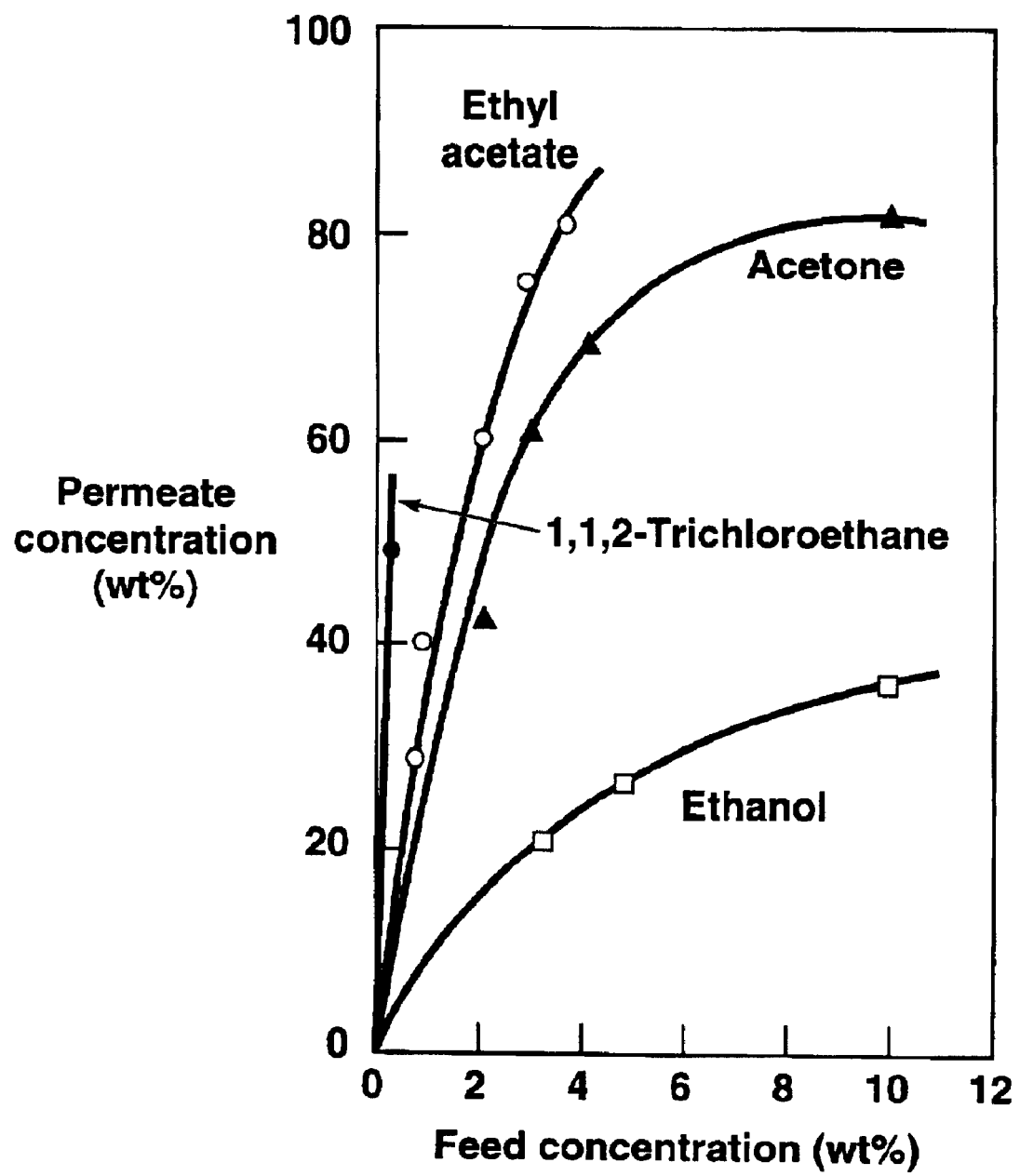
FIG. 3 is a graph of permeate concentration versus feed concentration for pervaporation experiments performed with aqueous solutions containing various organic compounds at concentrations up to 10 wt %.

The data collected from Examples 2–6, along with data for other organic-water separations obtained using silicone rubber membranes, are presented graphically in FIGS. 2 and 3. These Figures show the enrichment of organic achieved by pervaporation by comparing the organic concentration in the feed to the organic concentration in the permeate.

As can be seen in FIGS. 2 and 3, the enrichment of hydrophobic organics, such as 1,1,2-trichloroethane and chloroform, is much greater than that of hydrophilic organics, such as ethanol and acetone. Moderately hydrophobic organics, such as ethyl acetate, have moderate enrichments.

SET II—Dephlegmator Computer Simulations and Experiments

Example 8

Dephlegmator Computer Simulations

A series of computer calculation was performed with a modeling program, ChemCad V (ChemStations, Inc., Houston, Tex.), to illustrate the separation achieved by a dephlegmator. The calculations were performed assuming that the dephlegmator provides the equivalent of four vapor-liquid equilibrium stages, with approximately 10.9 kW of heat removal per stage. The feed to the dephlegmator was assumed to be a membrane permeate at 60° C. and 30 torr (0.6 psia), and to contain 35 wt % ethanol and 65 wt % water. The feed flow rate was assumed to be 100 kg/h. The calculations were performed to achieve different levels of ethanol concentration in the overhead vapor product from the dephlegmator.

Figure 4:
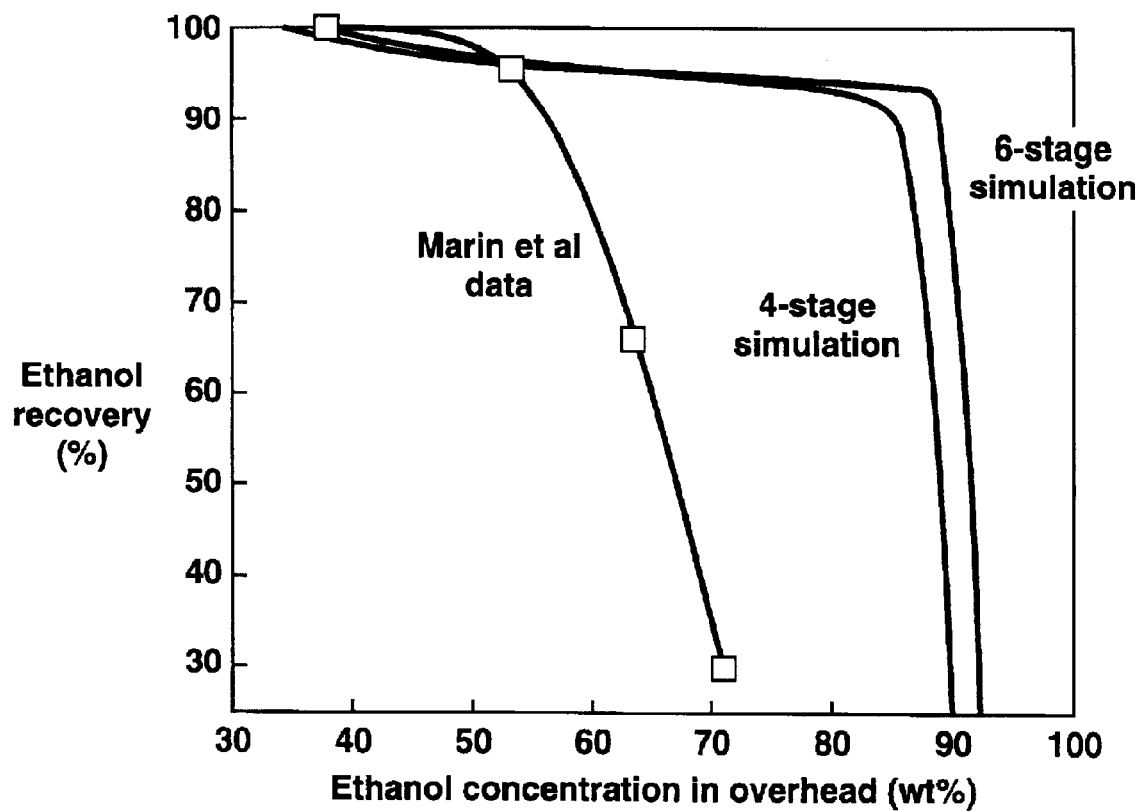
FIG. 4 is a graph showing the trade-off between ethanol recovery and product ethanol concentration for bioethanol production calculated by means of computer modeling.

The series of calculations was repeated assuming that the dephlegmator provides the equivalent of six vapor-liquid equilibrium stages. The results of the two series of calculations are shown in FIG. 4 in the form of curves showing the relationship between ethanol concentration and percent ethanol recovery in the overhead vapor product. As can be seen, the vapor can be enriched from about 35 wt % ethanol to between 85 and 90 wt % ethanol, while maintaining high levels of ethanol recovery.

Also shown on the graph for comparison is a plot of experimental data for ethanol recovery and ethanol concentration reported by Marin et al. ("Separation of volatile organic compounds from aqueous mixtures by pervaporation with multi-stage condensation," *J. Food Eng.*, 28, 225–238 (1996)). These data were obtained using fractional condensation in two sequential conventional partial condensation stages, one at 0 to –20° C. and the other at –20 to –80° C.

As can be seen, dephlegmation appears to offer the opportunity for improved separation performance, if the experimental results confirm the modeling calculations.

Examples 9–15

Dephlegmator Experiments

Experiments were performed with a brazed aluminum plate-fin heat exchanger, measuring 8"×9"×72" tall. The unit had eight vapor sections and nine coolant sections, and contained approximately 19 m$^2$ of vapor surface area. The dephlegmator was fed with a vapor at 60° C. containing 35 wt % ethanol and 65 wt % water, to simulate the permeate vapor from a pervaporation unit. A glycol solution was used as coolant, and the experiments were performed at varying coolant flow rates and temperatures. A vacuum pump was connected in the overhead line from the dephlegmator, as shown in FIG. 1, to pull a partial vacuum within the dephlegmator, to simulate the low pressure conditions on the permeate side of a pervaporation unit. The exhaust from the vacuum pump was condensed and passed to reservoirs for reuse.

Example 9

A series of experiments was performed with a feed vapor at 60° C. containing 35% ethanol and 65% water, and a feed flow rate to the dephlegmator of 2 kg/h. The dephlegmator vacuum pressure was 30 torr (0.6 psia). The coolant flow rate varied from 0.26 to 0.62 gpm (gallons per minute), and the coolant inlet temperature varied from about 9 to 19° C.

Figure 5:
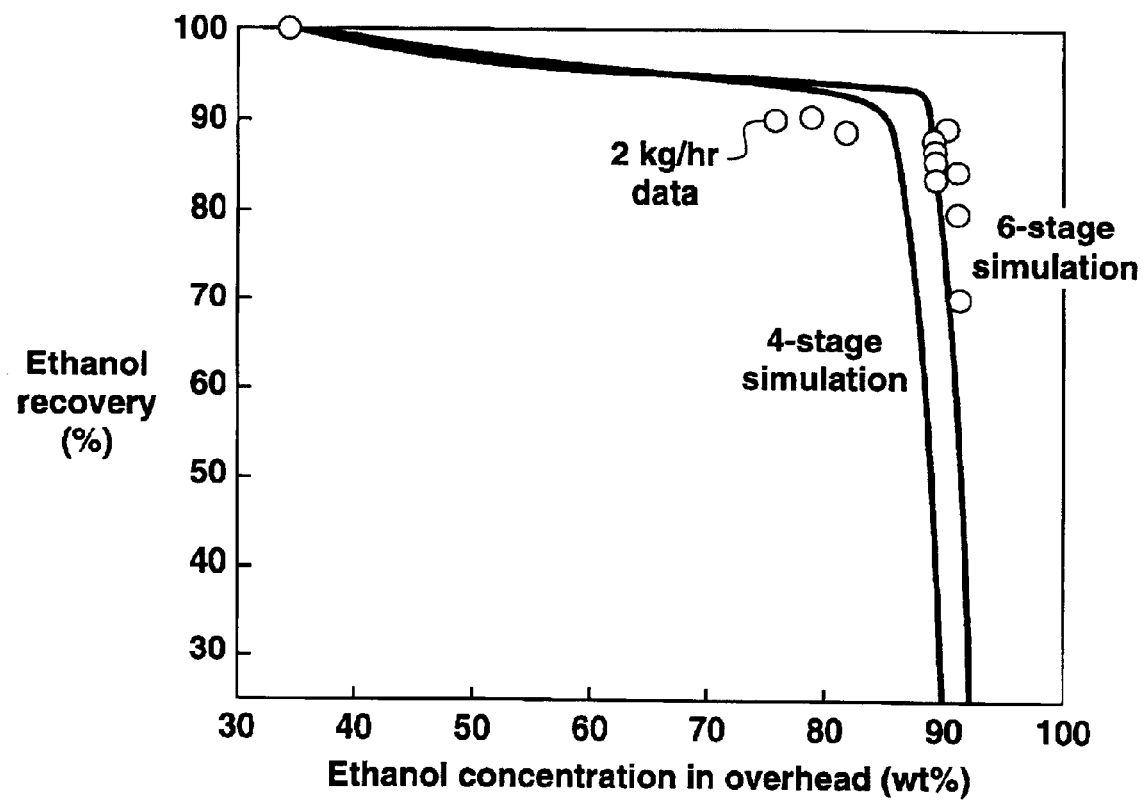
FIG. 5 is a graph showing the fit between experimental data and the computer modeling calculations, based on a feed flow rate of 2 kg/h through the dephlegmator.

The results of the experiment are shown in FIG. 5. As can be seen, the experimental data correspond well with the theoretical curve for a dephlegmator operation having the separation capability of six vapor-liquid equilibrium stages.

Example 10

Figure 6:
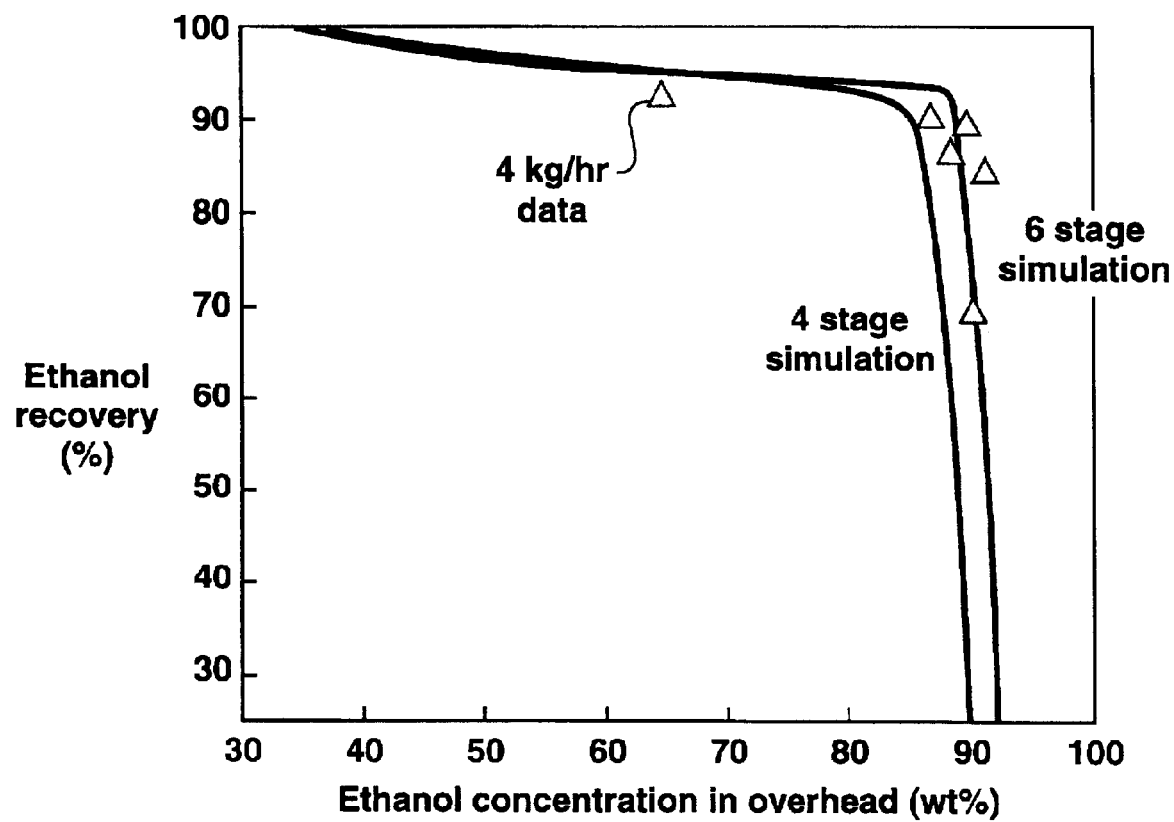
FIG. 6 is a graph showing the fit between experimental data and the computer modeling calculations, based on a feed flow rate of 4 kg/h through the dephlegmator.

A series of experiments was performed as in Example 9, except using a 4-kg/h feed flow rate to the dephlegmator. The results are shown in FIG. 6. Again, the experimental data match well with the theoretical curve corresponding to six separation stages.

Example 11

Figure 7:
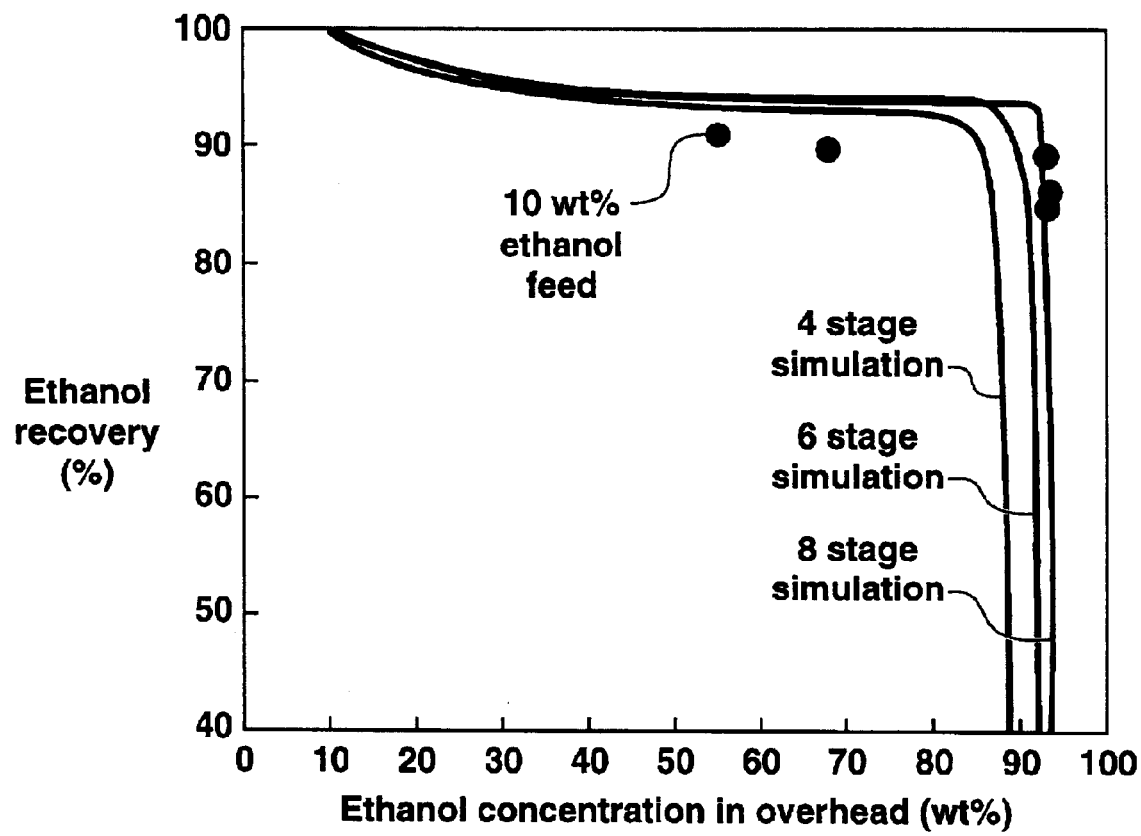
FIG. 7 is a graph showing the fit between experimental data and the computer modeling calculations, based on a feed ethanol concentration of 10 wt %.

A series of experiments was performed as in Example 9, except that the feed vapor had an ethanol concentration of only 10 wt %. The results are shown in FIG. 7. The experimental data match well with a theoretical curve corresponding to eight separation stages.

Example 12

Figure 8:
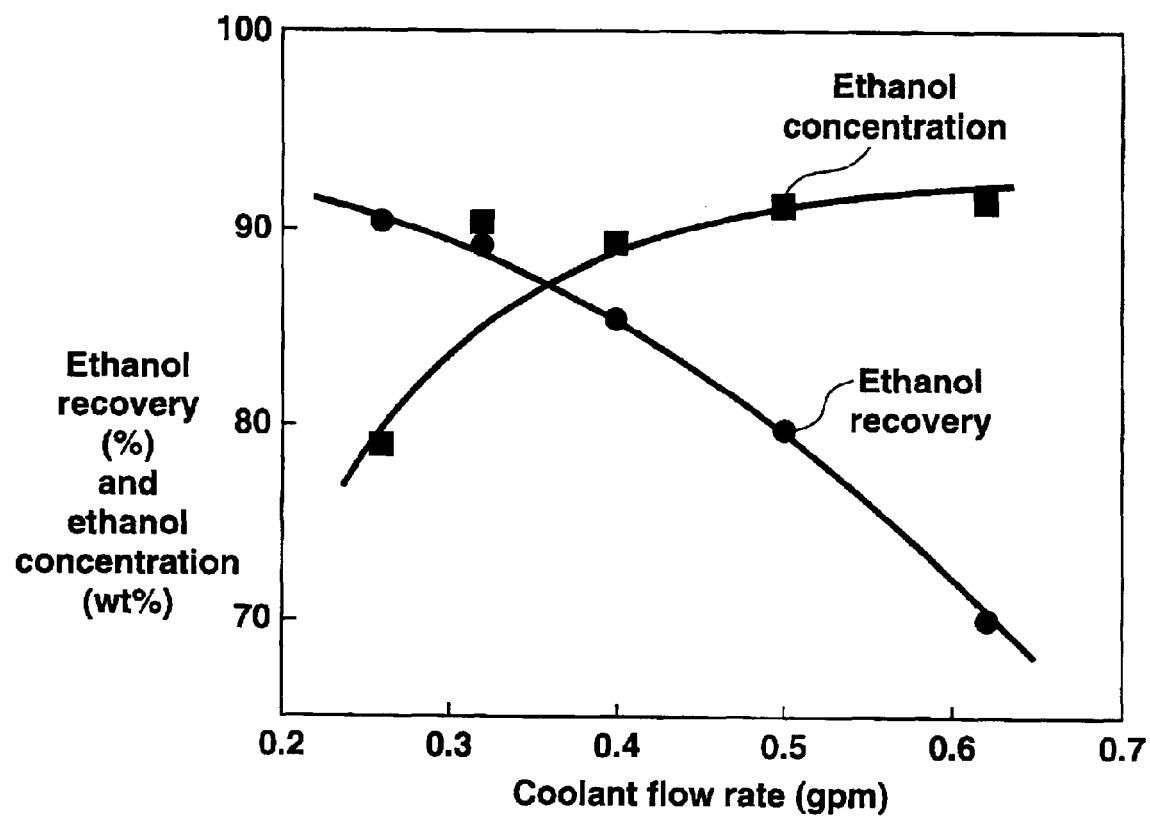
FIG. 8 is a graph showing the effect of coolant flow rate on ethanol recovery and ethanol product concentration.

Some of the data of Example 9 is presented again in FIG. 8, showing the ethanol concentration and percent ethanol recovery in the overhead vapor product as a function of coolant flow rate at a fixed coolant temperature of 9.2° C.

As can be seen, increasing the coolant flow rate increases the concentration of ethanol in the vapor product stream, but decreases the recovery of ethanol from the feedstream as the overhead product.

Example 13

Figure 9:
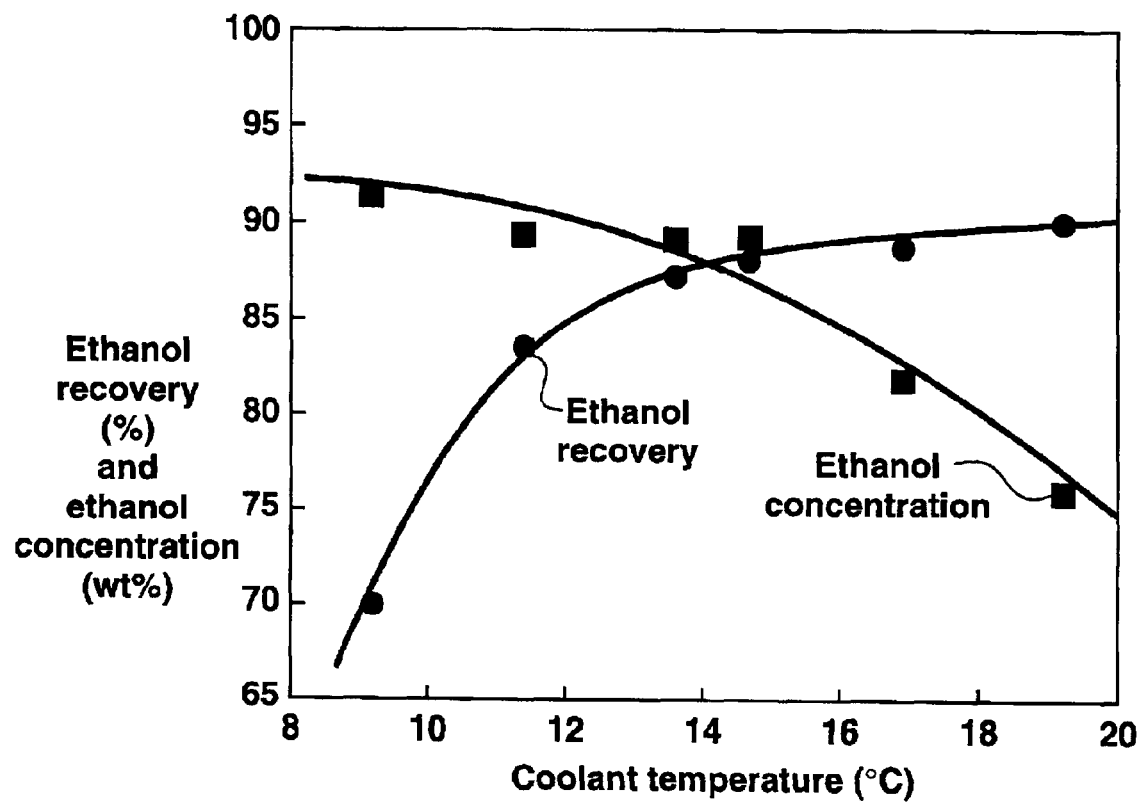
FIG. 9 is a graph showing the effect of coolant temperature on ethanol recovery and ethanol product concentration.

Some of the data of Example 9 is presented again in FIG. 9, showing the ethanol concentration and percent ethanol recovery in the overhead vapor product as a function of coolant temperature at a fixed coolant flow rate of 0.62 gpm.

As can be seen, increasing the coolant temperature increases the overall ethanol recovery, but decreases the concentration of ethanol in the vapor product stream.

Example 14

Figure 10:
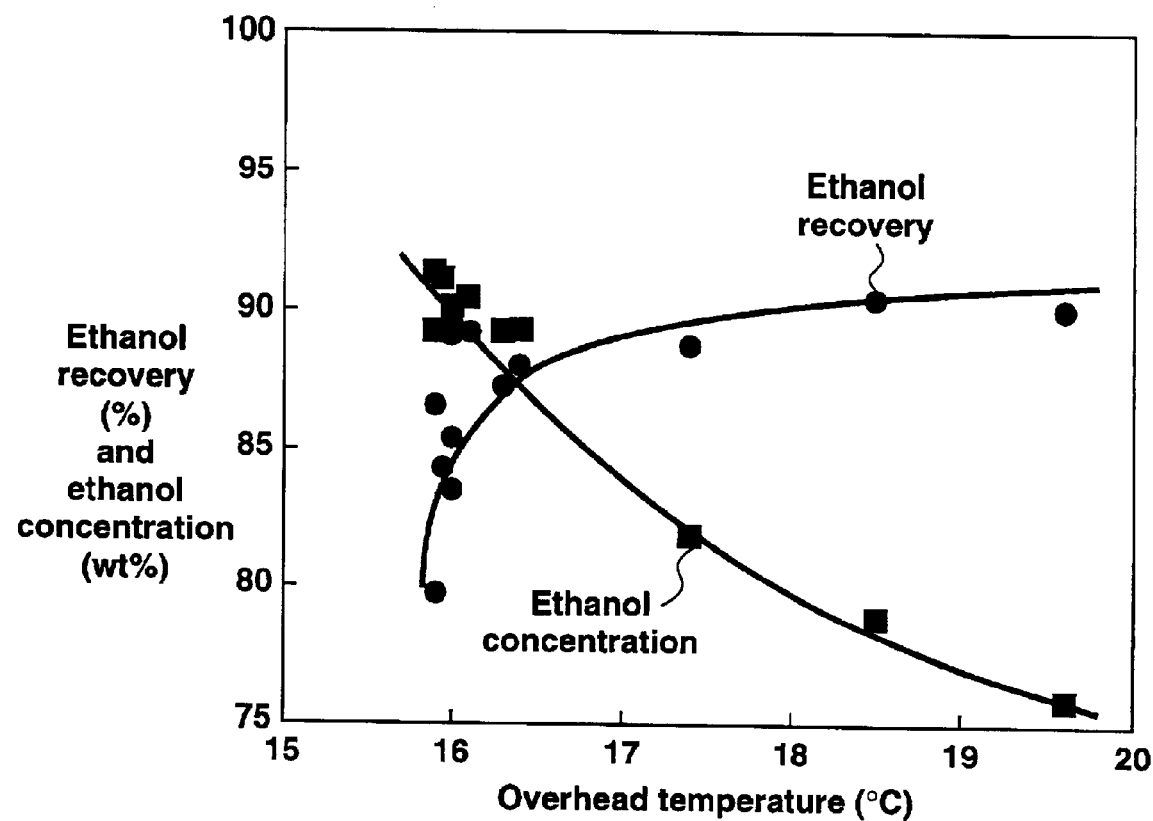
FIG. 10 is a graph showing the effect of dephlegmator overhead temperature on ethanol recovery and ethanol product concentration.

Varying the coolant temperatures and flow rates in the experiments in Example 9 also caused changes in the temperature of the ethanol vapor product stream. FIG. 10 shows the overall ethanol recovery and the concentration of ethanol in the overhead vapor product stream as a function of the product stream temperature.

As can be seen, the higher the product stream temperature is, the higher is the overall ethanol recovery, but the lower is the ethanol concentration in the product stream.

Example 15

Figure 11:
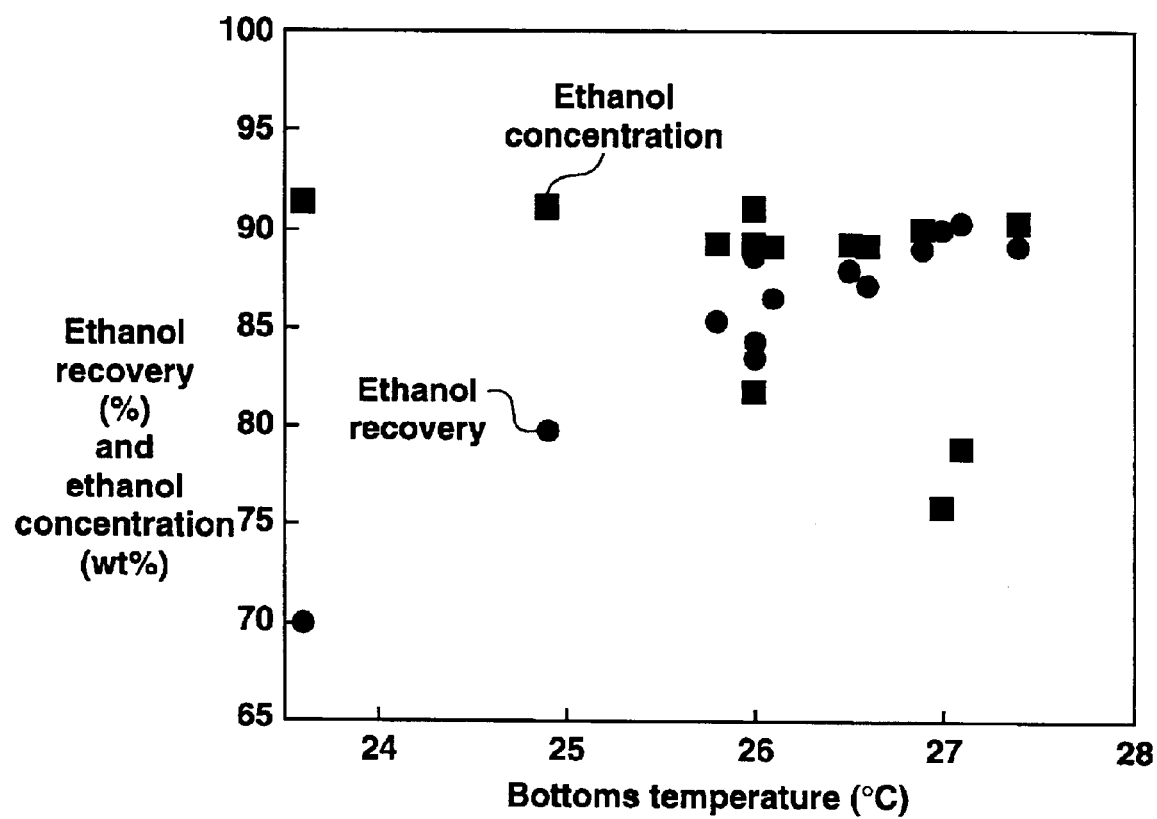
FIG. 11 is a graph showing the effect of dephlegmator bottom temperature on ethanol recovery and ethanol product concentration.

Varying the coolant temperatures and flow rates in the experiments in Example 9 also caused changes in the temperature of the dephlegmator bottoms stream. FIG. 11 shows the overall ethanol recovery and the concentration of ethanol in the overhead vapor product stream as a function of the dephlegmator bottoms stream temperature.

As can be seen, the higher the dephlegmator bottoms stream temperature is, the higher is the overall ethanol recovery.

SET 3:—Integrated Membrane-Dephlegmator Process Experiments

Experiments were performed with a small integrated membrane-dephlegmator test system to demonstrate the process of the invention. Four separate experiments were performed, each with one process parameter varied. Each experiment was performed twice. The integrated test system used the design of FIG. 1, as described above, including a vacuum pump to reduce the pressure on the permeate side of the pervaporation membranes.

Example 16

An experiment was performed with the integrated membrane-dephlegmator system. The feed to the membrane unit was approximately 5.1 wt % ethanol in water and the feed temperature was 40° C. The permeate pressure and the pressure throughout the dephlegmator system was maintained at approximately 31 torr (0.6 psia). The coolant was a glycol solution at 9° C., and the coolant flow rate through the dephlegmator was 0.26 gpm. The concentrations of ethanol in the permeate, the dephlegmator bottoms, and the dephlegmator overhead were measured, and the separation factors for the membrane step and for the integrated membrane-dephlegmator system overall were calculated. The results are shown in Table 3.

TABLE 3

| Total Permeate Flux (kg/m² · h) | Feed EtOH (wt %) [stream 101] | Permeate EtOH (wt %) [104] | Overhead EtOH (wt %) [109] | Bottoms EtOH (wt %) [108] | EtOH Recovery (%) | Separation Factor (Membrane Only) | Separation Factor (Membrane + Dephiegmator) |
|---|---|---|---|---|---|---|---|
| 0.19 | 5.1 | 31 | 91 | 5 | 90 | 8.5 | 182 |
| 0.19 | 5.0 | 29 | 90 | 5 | 88 | 7.6 | 168 |

As can be seen, the process incorporating pervaporation and dephlegmation is capable of providing the equivalent of pervaporation separation factor of between about 150 and 200.

Example 17

The experiment Example 16 was repeated, except that the permeate and dephlegmator system pressures were maintained at a higher pressure of 48 torr (0.9 psia). The feed to the membrane unit was approximately 4.9 wt % ethanol in water and the feed temperature was again 40° C. The coolant flow rate through the dephlegmator was again 0.26 gpm and the coolant temperature was 14° C. The results are shown in Table 4.

TABLE 4

| Total Permeate Flux (kg/m² · h) | Feed EtOH (wt %) [stream 101] | Permeate EtOH (wt %) [104] | Overhead EtOH (wt %) [109] | Bottoms EtOH (wt %) [108] | EtOH Recovery (%) | Separation Factor (Membrane Only) | Separation Factor (Membrane + Dephiegmator) |
|---|---|---|---|---|---|---|---|
| 0.11 | 4.9 | 28 | 93 | 13 | 63 | 7.7 | 267 |
| 0.12 | 4.8 | 33 | 94 | 12 | 74 | 9.9 | 304 |

As can be seen, the use of higher pressure in the dephlegmator system increases the concentration of ethanol in the dephlegmator overhead, but reduces the overall ethanol recovery compared to Example 16. The higher ethanol concentration in the overhead product means that in this case, the process provides a separation equivalent to a pervaporation separation factor of around 300.

Example 18

The experiment Example 16 was repeated, except that the coolant flow rate through the dephlegmator was increased to 0.32 gpm. The coolant temperature was 9° C. The feed to the membrane unit was 5.1 wt % ethanol in water and the feed temperature was again 40° C. The permeate and dephlegmator system pressures were maintained at 31 torr (0.6 psia). The results are shown in Table 5.

TABLE 5

| Total Permeate Flux (kg/m² · h) | Feed EtOH (wt %) [stream 101] | Permeate EtOH (wt %) [104] | Overhead EtOH (wt %) [109] | Bottoms EtOH (wt %) [108] | EtOH Recovery (%) | Separation Factor (Membrane Only) | Separation Factor (Membrane + Dephiegmator) |
|---|---|---|---|---|---|---|---|
| 0.19 | 5.1 | 31 | 92 | 6 | 86 | 8.4 | 267 |

TABLE 5-continued

| Total Permeate Flux (kg/m² · h) | Feed EtOH (wt %) [stream 101] | Permeate EtOH (wt %) [104] | Overhead EtOH (wt %) [109] | Bottoms EtOH (wt %) [108] | EtOH Recovery (%) | Separation Factor (Membrane Only) | Separation Factor (Membrane + Dephiegmator) |
|---|---|---|---|---|---|---|---|
| 0.19 | 5.1 | 30 | 92 | 6 | 85 | 8.1 | 210 |

Increasing the coolant flow rate to the dephlegmator slightly increases heat removal and, consequently, changes the ethanol concentration and recovery in the dephlegmator overhead. Compared to Example 16, the increased coolant flow rate through the dephlegmator increases the concentration of ethanol in the dephlegmator overhead, but reduces the overall ethanol recovery.

Example 19

The experiment of Example 16 was repeated, except that the feed temperature to the membrane unit was increased to 50° C. The membrane feed was again approximately 5.1 wt % ethanol in water. The coolant flow rate through the dephlegmator was increased to 0.55 gpm to provide effective cooling for the increased feed flow. The coolant temperature was 9° C. The permeate and dephlegmator system pressures were maintained at 31 torr (0.6 psia). The results are shown in Table 6.

TABLE 6

| Total Permeate Flux (kg/m² · h) | Feed EtOH (wt %) [stream 101] | Permeate EtOH (wt %) [104] | Overhead EtOH (wt %) [109] | Bottoms EtOH (wt %) [108] | EtOH Recovery (%) | Separation Factor (Membrane Only) | Separation Factor (Membrane + Dephiegmator) |
|---|---|---|---|---|---|---|---|
| 0.44 | 5.0 | 30 | 90 | 5 | 88 | 8.2 | 179 |
| 0.47 | 5.1 | 31 | 91 | 5 | 88 | 8.4 | 192 |

As can be seen, raising the temperature of the feed solution doubles the flux in the pervaporation step. Despite the resulting doubling of the feed flow to the dephlegmator, high levels of ethanol recovery at high ethanol concentration can be maintained by the process.

Example 20

Long-Term Integrated Process Experiment

The integrated membrane-dephlegmator system used for Examples 16–19 was used for another experiment to determine the ability of the system to perform consistently over a long period of time. The feed to the membrane unit was 5.1 wt % ethanol in water and the feed temperature was 40° C. The permeate pressure and the pressure throughout the dephlegmator system was maintained at approximately 31 torr (0.6 psia). The coolant flow rate through the dephlegmator was approximately 0.3 gpm and the coolant temperature was 9° C.

The concentrations of ethanol in the permeate, the dephlegmator bottoms, and the dephlegmator overhead were measured periodically over a 50-hour period. The data are shown in Table 7; the data are also represented graphically in FIG. 12, which shows the total permeate flux as a function of time, and in FIG. 13, which shows the ethanol concentration in the membrane permeate, the dephlegmator bottoms, and the dephlegmator overhead as a function of time.

TABLE 7

| Elapsed Time (h) | Total Permeate Flux (kg/m² · h) | Permeate EtOH (wt %) | Overhead EtOH (wt %) | Bottoms EtOH (wt %) | EtOH Recovery (%) |
|---|---|---|---|---|---|
| 18 | 0.18 | — | — | — | — |
| 21 | 0.19 | 31 | 92 | 6 | 86 |
| 24 | 0.19 | 30 | 92 | 6 | 85 |
| 41 | 0.19 | — | — | — | — |
| 44 | 0.19 | 31 | 91 | 5 | 90 |
| 47 | 0.19 | 29 | 90 | 5 | 88 |

Figure 12:
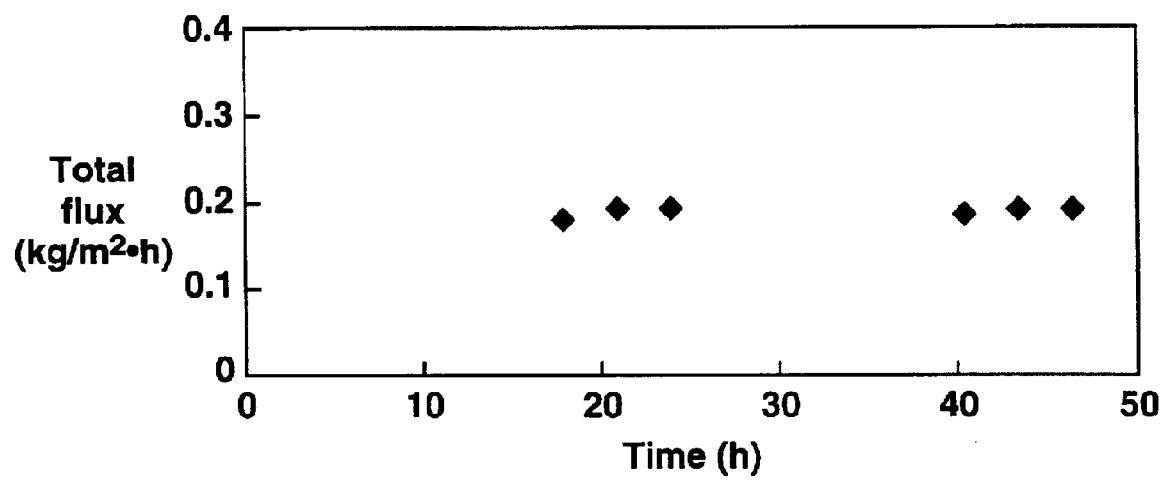
FIG. 12 is a plot showing the performance of a pervaporation/dephlegmation separation experiment in terms of permeate flux over a 50-hour period.
Figure 13:
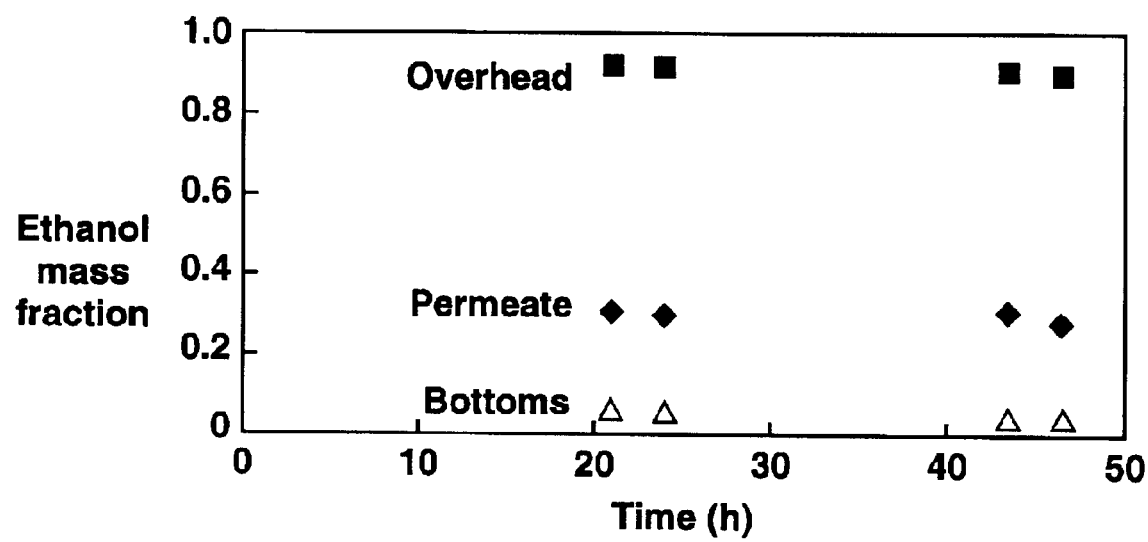
FIG. 13 is a plot showing the performance of a pervaporation/dephlegmation experiment in terms of ethanol concentration in the membrane permeate, the dephlegmator bottom product stream and the dephlegmator overhead product stream over a 50-hour period.

As can be seen in Table 7 and in FIGS. 12 and 13, the integrated membrane-dephlegmator system performed very consistently throughout the 50-hour test period.

SET 4:—Computer Simulations of Integrated Membrane-Dephlegmator Process

Example 21

A computer calculation was performed with a modeling program, ChemCad V (ChemStation, Inc., Houston, Tex.), to illustrate the performance of the integrated membrane-dephlegmator process for removing acetone from a wastewater stream from a chemical process or acetone production facility.

The process was assumed to use a design as in FIG. 1, with a condenser to recover the dephlegmator overhead in liquid form and a small vacuum pump positioned in line 116 to vent any non-condensable gases in the stream. The raw feed stream was assumed to contain 5 wt % of acetone in water at a feed flow rate of 20,000 kg/day. The membrane unit was assumed to be equipped with membranes providing a separation factor in favor of acetone over water. The permeate was assumed to be fed to a dephlegmator providing the equivalent of three vapor-liquid equilibrium stages. The dephlegmator bottoms stream was assumed to be recycled to the front of the process and mixed with stream 101.

The process was designed to produce a membrane residue water stream containing only 1,000 ppm acetone, suitable for discharge from the plant. This was calculated to require the use of 200 m² of membrane area.

The other results of the calculation are shown in Table 8.

TABLE 8

| | Stream | | | | |
|---|---|---|---|---|---|
| Parameter | Stream 101 | Stream 103 | Stream 104 | Stream 108 | Stream 115 |
| Flow Rate (kg/day) | 20,000 | 19,000 | 3,000 | 2,000 | 1,000 |
| Acetone Concentration (wt %) | 5.0 | 1,000 ppm | 33.0 | 0.5 | 98.0 |

Besides generating dischargeable water, the process yielded a 1,000 kg/day recovered acetone stream (stream 115) of 98% purity. Thus acetone recovery of 98% was achieved.

Example 22

A second calculation similar to the calculation of Example 21 was performed to illustrate the performance of the integrated membrane-dephlegmator process for recovering flavor concentrates lost from orange juice during concentration by evaporation.

The process was again assumed to use a design as in FIG. 1, with a condenser to recover the dephlegmator overhead in liquid form, a small vacuum pump positioned in line 116 to vent non-condensable gases, membranes with separation factor in favor of organics in the pervaporation step and the dephlegmator bottoms stream recycled to the front of the process. The raw feed stream was assumed to be water containing about 200 ppm of mixed aldehyde, alcohol and ester flavor essences, with an average volatility corresponding to ethyl acetate. The feed flow rate was assumed to be 200,000 kg/day, that is, 8,333 kg/h.

The process was designed to recover 97% of the flavors as concentrated flavor oil overhead product. This was calculated to require the use of 160 m$^2$ of membrane area.

The other results of the calculation are shown in Table 9.

TABLE 9

| | Stream | | | | |
|---|---|---|---|---|---|
| Parameter | Stream 101 | Stream 103 | Stream 104 | Stream 108 | Stream 115 |
| Flow Rate (kg/h) | 8,333 | 8,317 | 336 | 320 | 16 |
| Flavor Concentration (ppmw) | 200 | 5 | 5,000 | 50 | 10 wt % |

The process yielded a 16 kg/h stream of flavor oil, with a flavor essence concentration of 10 wt %. The membrane residue contained only about 5 ppm flavors.

We claim:

1. A process for treating a feed solution comprising an organic compound and water, the process comprising:
   (a) performing a membrane separation step selected from the group consisting of pervaporation and membrane distillation by:
      (i) providing a membrane having a feed side and a permeate side;
      (ii) passing the feed solution across the feed side;
      (iii) withdrawing a residue solution stream from the feed side;
      (iv) withdrawing a permeate vapor stream from the permeate side;
   (b) providing a dephlegmator having a coolant flow side and a gas stream flow side and adapted for partial condensation of a gas stream by providing countercurrent flow between the rising gas stream and a falling condensate stream;
   (c) passing at least a portion of the permeate vapor stream into the dephlegmator as a feed gas stream;
   (d) flowing a coolant across the coolant flow side in heat-exchanging relationship with the feed gas stream;
   (e) withdrawing a product vapor stream as an overhead stream from the dephlegmator;
   (f) withdrawing a product condensate stream as a bottom stream from the dephlegmator.

2. The process of claim 1, wherein the membrane separation step comprises a pervaporation step.

3. The process of claim 1, wherein the permeate vapor stream is enriched in the organic compound and the residue solution stream is depleted in the organic compound compared with the feed solution.

4. The process of claim 1, wherein the permeate vapor stream is enriched in the water and the residue solution stream is depleted in the water compared with the feed solution.

5. The process of claim 1, wherein the product vapor stream is enriched in the organic compound and the product condensate stream is depleted in the organic compound compared with the permeate vapor stream.

6. The process of claim 1, wherein the product vapor stream is enriched in the water and the product condensate stream is depleted in the water compared with the permeate vapor stream.

7. The process of claim 1, wherein the feed solution comprises an aqueous solution in which the organic compound is dissolved.

8. The process of claim 1, wherein the feed solution comprises an organic liquid in which water is dissolved.

9. The process of claim 1, wherein the feed solution further comprises at least one additional organic compound.

10. The process of claim 1, wherein the organic compound is selected from the group consisting of alcohols, aldehydes and ketones.

11. The process of claim 1, wherein the organic compound is ethanol.

12. The process of claim 1, wherein the organic compound is acetone.

13. The process of claim 1, wherein the organic compound is a flavor compound.

14. The process of claim 1, wherein the feed solution is an aqueous solution comprising no more than about 10 wt % of the organic compound.

15. The process of claim 1, wherein the feed solution arises from bioethanol production.

16. The process of claim 1, wherein the dephlegmator is a shell-and-tube dephlegmator.

17. The process of claim 1, wherein the dephlegmator is a plate-fin dephlegmator.

18. The process of claim 1, wherein the dephlegmator includes at least a section containing structured packing.

19. The process of claim 1, wherein the concentration of the organic compound in the product vapor stream is at least about 85 wt %.

20. The process of claim 1, wherein the product vapor contains at least about 85% of the organic compound that was present in the feed solution.

21. The process of claim 1, wherein the residue solution stream contains at least about 99 wt % organic compound.

22. The process of claim 1, wherein the coolant is water.

23. The process of claim 1, wherein the membrane is a polymeric membrane.

24. The process of claim 1, wherein the membrane is an inorganic membrane.

25. The process of claim 1, further comprising heating the feed solution before passing it across the feed side.

26. The process of claim 1, further comprising drawing a partial vacuum on the permeate side by means of a vacuum pump.

27. The process of claim 1, further comprising passing a sweep gas across the permeate side.

28. The process of claim 1, further comprising condensing the product vapor stream to form a liquid product.

29. The process of claim 1, further comprising subjecting the product vapor stream to additional purification by passing at least a portion of the product vapor stream to a further treatment step selected from the group consisting of pervaporation, dephlegmation, distillation, condensation, phase separation, evaporation, stripping, scrubbing, absorption and adsorption.

30. The process of claim 1, further comprising subjecting the product vapor stream to additional purification by distillation.

31. The process of claim 1, further comprising subjecting the product vapor stream to additional purification by pervaporation.

32. The process of claim 1, further comprising subjecting the product vapor stream to additional purification by dephlegmation.

33. The process of claim 28, further comprising recirculating the liquid product as additional feed solution to step (a).

34. The process of claim 1, wherein the membrane separation step comprises a membrane distillation step.

35. A process for treating a feed vapor comprising an organic compound and water, the process comprising:
    (a) providing a vapor separation membrane having a feed side and a permeate side;
    (b) passing the feed vapor across the feed side;
    (c) withdrawing a residue vapor stream from the feed side;
    (d) withdrawing a permeate vapor stream from the permeate side;
    (e) providing a dephlegmator having a coolant flow side and a gas stream flow side and adapted for partial condensation of a gas stream by providing countercurrent flow between the rising gas stream and a falling condensate stream;
    (f) passing at least a portion of the permeate vapor stream into the dephlegmator as a feed gas stream;
    (g) flowing a coolant across the coolant flow side in heat-exchanging relationship with the feed gas stream;
    (h) withdrawing a product vapor stream as an overhead stream from the dephlegmator;
    (i) withdrawing a product condensate stream as a bottom stream from the dephlegmator.

36. The process of claim 35, wherein the permeate vapor stream is enriched in the organic compound and the residue vapor stream is depleted in the organic compound compared with the feed vapor.

37. The process of claim 35, wherein the permeate vapor stream is enriched in the water and the residue vapor stream is depleted in the water compared with the feed vapor.

38. The process of claim 35, wherein the product vapor stream is enriched in the organic compound and the product condensate stream is depleted in the organic compound compared with the permeate vapor stream.

39. The process of claim 35, wherein the product vapor stream is enriched in the water and the product condensate stream is depleted in the water compared with the permeate vapor stream.

40. The process of claim 35, wherein the feed vapor further comprises at least one additional organic compound.

41. The process of claim 35, wherein the organic compound is ethanol.

42. The process of claim 35, wherein the organic compound is acetone.

43. The process of claim 35, wherein the organic compound is a flavor compound.

44. The process of claim 35, wherein the dephlegmator is a shell-and-tube dephlegmator.

45. The process of claim 35, wherein the dephlegmator is a plate-fin dephlegmator.

46. The process of claim 35, wherein the dephlegmator includes at least a section containing structured packing.

47. The process of claim 35, wherein the concentration of the organic compound in the product vapor stream is at least about 85 wt %.

48. The process of claim 35, wherein the product vapor contains at least about 85% of the organic compound that was present in the feed vapor.

49. The process of claim 35, wherein the coolant is water.

50. The process of claim 35, wherein the membrane is a polymeric membrane.

51. The process of claim 35, wherein the membrane is an inorganic membrane.

52. The process of claim 35, further comprising heating the feed vapor before passing it across the feed side.

53. The process of claim 35, further comprising drawing a partial vacuum on the permeate side by means of a vacuum pump.

54. The process of claim 35, further comprising passing a sweep gas across the permeate side.

55. The process of claim 35, further comprising condensing the product vapor stream to form a liquid product.

56. The process of claim 35, further comprising subjecting the product vapor stream to additional purification by passing at least a portion of the product vapor stream to a further treatment step selected from the group consisting of membrane separation, dephlegmation, distillation, condensation, phase separation, evaporation, stripping, scrubbing, absorption and adsorption.

57. The process of claim 35, further comprising subjecting the product vapor stream to additional purification by distillation.

58. The process of claim 35, further comprising subjecting the product vapor stream to additional purification by membrane separation.

59. The process of claim 35, further comprising subjecting the product vapor stream to additional purification by dephlegmation.

60. A fermentation process, comprising:
    (a) performing a fermentation step, comprising:
        (i) introducing a biomass into a fermentation reactor;
        (ii) fermenting the biomass, thereby forming a fermentation broth comprising the biomass and a fermentation product;
    (b) withdrawing a portion of the fermentation broth from the fermentation reactor;
    (c) performing a pervaporation separation step, comprising:
        (i) providing a membrane having a feed side and a permeate side;
        (ii) passing the portion of the fermentation broth as a feed solution across the feed side;
        (iii) withdrawing a residue solution stream from the feed side;
        (iv) withdrawing a permeate vapor stream from the permeate side;

(d) providing a dephlegmator having a coolant flow side and a gas stream flow side and adapted for partial condensation of a gas stream by providing countercurrent flow between the rising gas stream and a falling condensate stream;

(e) passing at least a portion of the permeate vapor stream into the dephlegmator as a feed gas stream;

(f) flowing a coolant across the coolant flow side in heat-exchanging relationship with the feed gas stream;

(g) withdrawing a product vapor stream as an overhead stream from the dephlegmator;

(h) withdrawing a product condensate stream as a bottom stream from the dephlegmator.

61. The process of claim 60, wherein the permeate vapor stream is enriched in the fermentation product and the residue solution stream is depleted in the fermentation product compared with the feed solution.

62. The process of claim 60, wherein the product vapor stream is enriched in the fermentation product and the product condensate stream is depleted in the fermentation product compared with the permeate vapor stream.

63. The process of claim 60, wherein the fermentation broth further comprises at least one additional fermentation product.

64. The process of claim 60, wherein the fermentation product is selected from the group consisting of alcohols, aldehydes, ketones, organic acids and flavor compounds.

65. The process of claim 60, wherein the fermentation product is ethanol.

66. The process of claim 60, wherein the fermentation product is acetone.

67. The process of claim 60, wherein the fermentation product is a flavor compound.

68. The process of claim 60, wherein the biomass is corn.

69. The process of claim 60, further comprising heating the feed solution before passing it across the feed side.

70. The process of claim 60, further comprising condensing the product vapor stream to form a liquid product.

71. The process of claim 60, further comprising subjecting the product vapor stream to additional purification by passing at least a portion of the product vapor stream to a further treatment step selected from the group consisting of pervaporation, dephlegmation, distillation, condensation and phase separation.

72. The process of claim 60, wherein during step (a)(i) the biomass is introduced into the fermentation reactor on a batch basis.

73. The process of claim 60, wherein during step (a)(i) the biomass is introduced into the fermentation reactor on a continuous basis.

74. The process of claim 60, wherein the residue solution stream is recirculated to step (a).

75. The process of claim 60, wherein the product condensate stream is recirculated to step (a).

76. The process of claim 60, wherein the product condensate stream is recirculated to step (c).

* * * * *